US008222385B2

(12) United States Patent
Yoshizaki et al.

(10) Patent No.: US 8,222,385 B2
(45) Date of Patent: Jul. 17, 2012

(54) GERM CELL MARKER USING FISH VASA GENE

(75) Inventors: Goro Yoshizaki, Tokyo (JP); Yutaka Takeuchi, Tokyo (JP); Kazue Nagasawa, Tokyo (JP); Kentaro Higuchi, Tokyo (JP); Tetsuro Morita, Oita (JP); Naoki Kabeya, Tokyo (JP)

(73) Assignees: National University Corporation Tokyo University of Marine Science Technology (JP); Nippon Suisan Kaisha, Ltd. (JP)

( * ) Notice: Subject to any disclaimer, the term of this patent is extended or adjusted under 35 U.S.C. 154(b) by 122 days.

(21) Appl. No.: 12/532,304

(22) PCT Filed: Mar. 26, 2008

(86) PCT No.: PCT/JP2008/000743
§ 371 (c)(1),
(2), (4) Date: Jan. 12, 2010

(87) PCT Pub. No.: WO2008/129838
PCT Pub. Date: Oct. 30, 2008

(65) Prior Publication Data
US 2010/0132056 A1 May 27, 2010

(30) Foreign Application Priority Data

Mar. 26, 2007 (JP) ................................ 2007-080022

(51) Int. Cl.
*C07H 21/04* (2006.01)
*C07H 21/02* (2006.01)
*C12N 5/00* (2006.01)
*C12N 5/02* (2006.01)
*A01K 67/027* (2006.01)

(52) U.S. Cl. ......... 536/23.5; 536/23.1; 435/325; 800/20
(58) Field of Classification Search .................. 536/23.1
See application file for complete search history.

(56) References Cited

FOREIGN PATENT DOCUMENTS
WO         02/29064 A2    4/2002

OTHER PUBLICATIONS

Yoshizaki, Fish Physiology and Biochemistry, 2002, 26:3-12.*
Kennell,. 1971, Progr. Nucl. Acid. Res, 11:259-301.*
Cardinali, M., et al., "Hormonal Regulation of Vasa-Like Messenger RNA Expression in the Ovary of the Marine Teleost Sparus aurata" Biology of Reproduction (2004), 70:737-743.
Knaut, H., et al., "An Evolutionary Conserved Region in the vasa 3'UTR Targets RNA Translation to the Germ Cells in the Zebrafish," Current Biology (2002), 12:454-466.
Kobayashi, T., et al., "Differential expression of vasa homologue gene in the germ cells during oogenesis and spermatogenesis in a teleost fish, tilapia, Oreochromis niloticus," Mechanisms of Development (2000), 99:139-142.
Nagasawa, K., et al., "Expression Analysis of vasa Gene in the Genital Glad of a Preserved Bluefin Tuna," Abstracts for the Annual Meeting of the Japanese Society of Fisheries Science, Sep. 25, 2007, vol. 2007, No. 714, p. 94.
Okutsu, T., et al., "Testicular germ cells can colonize sexually undifferentiated embryonic gonad and produce functional eggs in fish," PNAS (2006), 103:2725-2729.
Takeuchi, Y., et al., "Applying Spermatogonium Transplantation Technique among Difference Marine Fish Species," Abstracts for the Annual Meeting of the Japanese Society of Fisheries Science, Mar. 28, 2007, vol. 2007, No. 319, p. 43.
Wu, G.-C., et al., "Vasa Protein" Swissprot, Accession Q27ID5, (Oct. 31, 2006), retrieved from the internet: http://www.ncbi.nlm.nih.gov/protein/123891708.
Xu, H., et al., "Differential Expression of vasa RNA and Protein During Spermatogenesis and Oogenesis in the Gibel Carp (*Carassius auratus* gibelio), a Bisexually and Gynogenetically Reproducing Vertebrate," Developmental Dynamics (2005), 233:872-882.
Yoshizaki, G., et al., "Cloning and characterization of a vasa-like gene in rainbow trout and its expression in the germ cell lineage," Molecular Reproduction and Development (2000), 55:364-371.
Yoshizaki, G., et al., "Green Fluorescent Protein Labeling of Primordial Germ Cells Using a Nontransgenic Method and Its Application for Germ Cell Transplantation in Salmonidae" Biology of Reproduction (2005), 73:88-93.
Yoshizaki, G., "Developmental Biotechnology Using Germ Cell Transplantation in Salmonids," Nippon Suisan Gakkaishi (2006), 72:954-955.
Liang, L., et al, "Localization of vasa protein to the *Drosophila* pole plasm is independent of its RNA-binding and helicase activities," Development (1994), 120:1201-1211.
Rongo, C., et al., "Localization of oskar RNA regulates oskar translation and requires Oskar protein," Development (1995), 121:2737-2746.
Extended European Search Report for 0872622.3 dated Mar. 8, 2010.
Database EMBL Accession No. DQ174775 retrieved Feb. 22, 2010.
Raz, E., "The function and regulation of vasa-like genes in germ-cell development," Genome Biology (2000), 1:1017.1-1017.6.

* cited by examiner

*Primary Examiner* — Valarie Bertoglio
(74) *Attorney, Agent, or Firm* — Chainey P. Singleton; Edwin S. Flores; Chalker Flores, LLP

(57) ABSTRACT

In order to examine whether or not a germ cell derived from a donor fish, which has been transplanted into a recipient fish of a different species by a surrogate fish technique, grows or matures in the gonad of the recipient fish, it is necessary to use, as an indicator, a trait that is specifically expressed in the germ cell and can be used to distinguish the recipient fish from the donor fish. Vasa gene, which is a germ cell-specific gene, is specific to a primordial germ cell and a spermatogonium/an oogonium, and it is not expressed in a somatic cell. In the present invention, the Vasa gene sequences of a tuna, a chub mackerel, a spotted mackerel, an eastern little tuna, and a drumfish are determined, and the expression of such gene is used as a marker for a germ cell. In addition, according to the present invention, it is possible to specifically detect only a tuna Vasa gene in Vasa gene sequences that are highly conserved in fishes, without sequencing. Thus, a tuna-derived germ cell can be reliably and simply identified in the gonad of the recipient fish. As a result, the growth or breeding of tuna can be carried out with good efficiency. Moreover, utilizing the aforementioned findings, even in a case in which not only a tuna but also another Perciformes fish is used as a donor, a germ cell derived from the donor fish can be efficiently detected from the gonad of a recipient fish of a different species.

4 Claims, 6 Drawing Sheets

Detection of bluefin tuna vasa mRNA using
in situ hybridization method 2-year-old bluefin tuna testis Difference in stainability between bluefin tuna germ cell and
drumfish germ cell, which was examined using in situ hybridization method

Figure 3 Recognition sites of primers used in detection of tuna vasa cDNA and restriction enzyme sites

| | |
|---|---|
| Bluefin tuna vasa cDNA | CAGACACATTTA TCCAA GTCAC AAAGT TCTCC AAGA GGAGAGCAG TCCTT GACCTCCTGAAG 1440 |
| Drumfish vasa cDNA | CAGACACATTTG TCCAA GTCAC AAAGT TCTCC AAGA GGAGAGCAA CTCCT GACCTCCTGAAG 648 |

1st primer fw

| | |
|---|---|
| | ACCACT GGAACGGAGCGCACC ATGGTGTTTG TAGAGACCAAG ACCAAGCAAGCTGATTTT AT 1499 |
| | ACAACTGGGAACGGAACGCGCA CCATGGTGTTTG TGGAGACCAAG ACCAAGCAAGCTGATTAT 708 |

| | |
|---|---|
| | TGCCACGTTCTT GTGCCAGAGAAAGTTC AACTTCCGC TGG CAGACCATTCA GGTGACCGAGAGCA 1559 |
| | CGCGACCGTACCTGTGCCAGAGAAAGTTC AACCAGACCATTCAACG CGACCGTCAGCA 768 |

Nested primer fw

| | |
|---|---|
| | GCGGAGCGGAGAGCAAGGCTCTGGCAGACTTCCGCTGG TTAATGTCCAGTCCTAGTAGC 1619 |
| | GCGGAGCGGAGCAAGGCTCTGGCAGACTTCCGCTGG CTAGCCAGTCTCAGTCCTGGTGC 828 |

Bluefin tuna vasa specific Hpa I site

| | |
|---|---|
| | AACCCTCGTAGCTGCCC CGGTTTGATATTCCAGATTCTACGTAACATGTCTATGAGTTTGA 1679 |
| | GACCTCGTAGCTGCCCGTGGTCTTGATGTTCCCGGCTACTGAGGTGTCTATGGCTTTGA 888 |

1st primer rv

| | |
|---|---|
| | CCTCCCAACACATTGATA AATATGTCCACCGTATTGGGAGGAGCCGCTGCG AA 1739 |
| | CCTCCCAACAACATCAGAATAATATGTCCACCGGATTGGGAGGACCCGCCGGTGCGG AA 948 |

| | |
|---|---|
| | CACAGGGAGGCATCAC AGTCAGTCCCAAGCCCAGCAGGAAGTGCCTTCATGGCTCGTCCTTT 1799 |
| | CACTGGCAGAGCGTCAGTCCTGTCCAAGCCCAGCAGGAAGTGCCTCGGTGGCTCGCCGCT 1008 |

Nested primer rv

| | |
|---|---|
| | GGTCACAGTCCAAGCCCAGCAGGAAGTGCCTTCATGGCTCGTCCTT GCCGTT 1859 |
| | CGTCACAGTTCCTGTCCAAGCCCAGCAGGAAGTGCCTCGGTGGCTCGCCGCT 1068 |

Bluefin tuna vasa cDNA
(Seq ID No: 1, positions 1381-1859)
Drumfish vasa cDNA
(Seq ID No: 18, positions 589-1068)

- Number of nucleotides in fragments amplified by PCR
  1st PCR···357bp  Nested PCR···179bp
- After treatment with Hpa I, a tuna vasa sequence (179 bp) is divided into fragments of 146 bp and of 33 bp.

Figure 4-1

PCR products and restriction enzyme treatments using cDNA as template

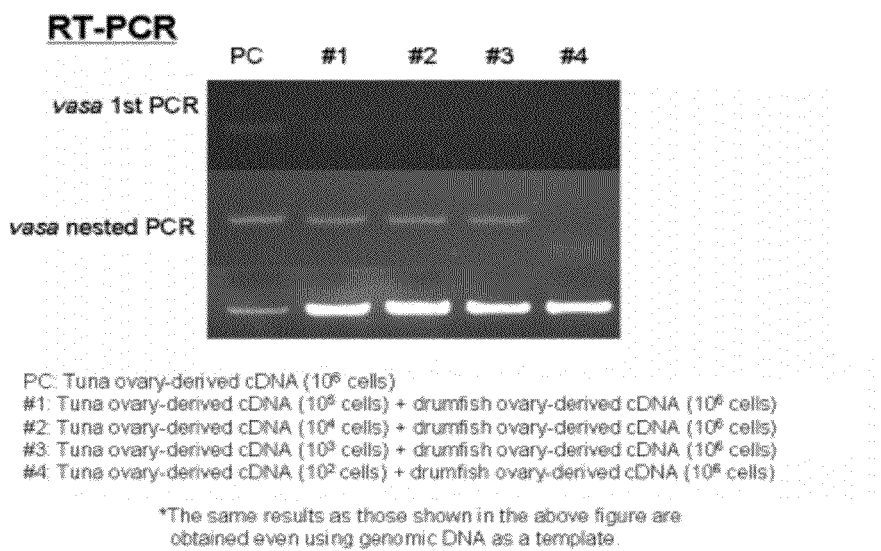

PC: Tuna ovary-derived cDNA ($10^6$ cells)
1: Tuna ovary-derived cDNA ($10^6$ cells) + drumfish ovary-derived cDNA ($10^6$ cells)
2: Tuna ovary-derived cDNA ($10^4$ cells) + drumfish ovary-derived cDNA ($10^6$ cells)
3: Tuna ovary-derived cDNA ($10^3$ cells) + drumfish ovary-derived cDNA ($10^6$ cells)
4: Tuna ovary-derived cDNA ($10^2$ cells) + drumfish ovary-derived cDNA ($10^6$ cells)

*The same results as those shown in the above figure are obtained even using genomic DNA as a template.

PCR products and restriction enzyme treatments using cDNA as template

Hpa I treatment of PCR products

Analysis of genital gland of drumfish (surrogate) into which bluefin tuna germ cell has been transplanted

Figure 6

It corresponds to the position at 1070 bp of entire length bluefin tuna vasa cDNA.

Bluefin (Seq ID No: 1, positions 1462-1819), Nibe (Seq ID No: 9, positions 1418-1775), Saba (Seq ID No: 23), Suma (Seq ID No: 24)

Figure 7
Tuna vasa PCR using ovary of spotted mackerel and ovary of eastern little tuna
1: PCR
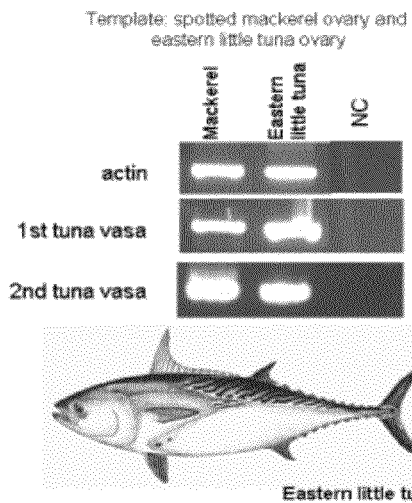
2: Restriction enzyme (HpaI) treatment
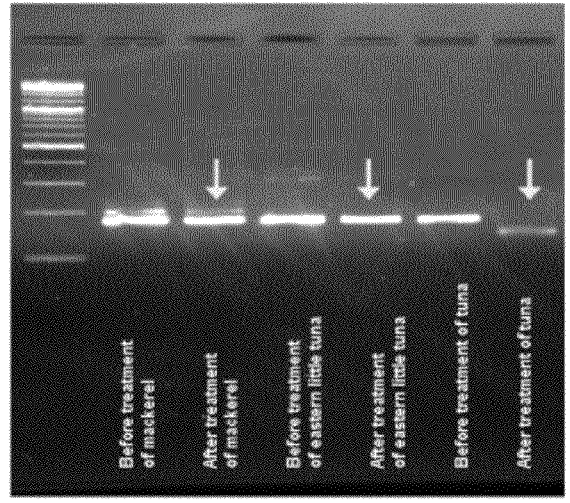

GERM CELL MARKER USING FISH VASA GENE

TECHNICAL FIELD

The present invention relates to: a Vasa protein of Perciformes fish such as tuna; a Vasa gene of Perciformes fish such as tuna; a method for detecting the germ cell of Perciformes fish such as tuna, using such Vasa protein or Vasa gene as a target; a method for evaluating the growth and/or maturation of the germ cell of a Perciformes donor fish such as a tuna, which has been transplanted into a recipient fish of a different species, utilizing the aforementioned detection method; and the like.

BACKGROUND ART

By gene analysis using *Drosophila*, it became clear that Oskar, Vasa, Tudor, and Nanos genes have core functions in the determination mechanism of germ cells (for example, Rongo, C., et al., Development, 121, 2737-2746, 1995). These genes are all accumulated in polar granule in the formation of egg cells, and this blastomere having a maternal determination factor determines germ cell destiny. It is considered that Vasa gene encodes ATP-dependent RNA helicase and that its functions are associated with regulation of translation from mRNA to a protein (for example, Liang, L., et al, Development, 120, 1201-1211, 1994). In addition, a structure for its enzymatic function is evolutionally strongly conserved. Thus, Vasa homolog genes have been identified in many multicellular animal species ranging from Platyhelminthes (planarian) to humans.

Based on the aforementioned findings, as a method for simply sorting a cell having germ cell differentiation potency using, as an indicator, the expression of a marker gene, without performing complicated operations such as homologous recombination, there has been reported a method for obtaining a germ cell, which comprises recovering a cell having germ cell differentiation potency from a transgenic non-human mammal, into which a recombinant expression vector comprising a marker gene incorporated therein such that it is under the control of the promoter sequence of a Vasa homolog gene derived from the mammal has been introduced, using the expression of the marker gene as an indicator (for example, Japanese Laid-Open Patent Application Nos. 2006-333762 and 2003-235558).

On the other hand, primordial germ cell is an original cell for egg and sperm, which is modified to an individual via processes of maturation and fertilization. There has been known a method for inducing the differentiation of a separated primordial germ cell derived from fish into a germ cell line, which comprises transplanting the fish-derived separated primordial germ cell into the early embryo of a recipient fish of a different species, and particularly transplanting the separated primordial germ cell into the peritoneal cavity of a recipient fish of a different species at the early development stage (for example, Japanese Patent Laid-Open Nos. 2006-333762 and 2003-235558).

At present, in cultivation of tuna, a method in which native juvenile fish (in general, several tens of to several hundreds of gram) are captured by a fisher and grown has been mainly applied. In recent years, the amount of native tuna caught has been reduced, and thus catch quotas for mature tuna have been strictly limited. Hence, a stable supply of juvenile fish would not be guaranteed in the future by a method of obtaining such juvenile fish from nature. In addition, as in the case of salmon and *Pagrus major*, if a technique of artificial seedling production was established, it would be expected that breeding can be carried out by alternation of generations, while selecting parent fish having good traits, and that juvenile fish having stable quality can be supplied with better cultivation efficiency. The mechanism of maturation of tuna has not yet been sufficiently clarified. However, it is considered that tuna reaches initial maturation after its body weight has exceeded several tens of kilograms. Since the body size of tuna is large, differing from other fish species, it is grown by a seedling production by a method of collecting fertilized eggs naturally laid by parent fish in a preserve or in an enclosed bay using a finely-woven net. Since *Pagrus major* and the like lay eggs in a water tank, a device for collecting the eggs with a net by overflowing seawater on the surface of the tank can be easily produced. However, when such operation is carried out at sea, it is very troublesome.

When specific individual fishes are to be mated for the purpose of breeding or the like, artificial egg collection is carried out by squeezing the abdomen of a mother fish, sperm is also collected in the same manner, and the collected egg and sperm are then subjected to artificial insemination. However, in a case in which parent fishes are large in size, like tuna, this method is not easy. Moreover, in the industrial field, for the purpose of controlling shipment time and fish cultivation period, it is possible to enhance profitability by shifting the time at which juvenile fish is produced. Therefor, it is necessary to control water temperature and photoperiod in a place where parent fishes can be environmentally controlled, so as to shift the season, thereby controlling the time at which the parent fishes lay eggs. However, in a case in which parent fishes are large in size, like tuna, enormous manpower and costs are required.

Surrogate fish technique is a technique of allowing fish species that are suitable for seedling production to produce the gametes of fish species that are unsuitable for seedling production, or to lay eggs and then to be subjected to insemination, so as to simply allow seedling production at low costs. For example, if the surrogate fish technique described in the aforementioned Patent Document 2 is applied to tuna, so as to allow small-sized fish species used as recipient fishes to maturate tuna-derived germ cells, full cultivation including seedling production can be achieved in a small water tank, and it is expected to result in significant laborsaving and cost reduction. In transplanting a separated primordial germ cell, it is necessary to propagate tuna-derived primordial germ cells incorporated into the gonad of a recipient and to detect the ratio between recipient-derived germ cells and donor-derived germ cells. It is an object of the present invention to provide a method for inducing the differentiation of a primordial germ cell into a germ cell line, which comprises transplanting a primordial germ cell derived from a Perciformes donor fish such as a tuna into the early embryo of a recipient fish of a different species, wherein ovum and/or sperm derived from the donor fish are specifically detected, and such donor fish-derived ovum and/or sperm are then distinguished from germ cells derived from the recipient fish.

The present inventors have succeeded in producing a rainbow trout from a masu salmon (*Oncorhynchus masou*) by carrying out heteroplastic germ cell transplantation on Salmonidae fish. In this transplantation, a genetically modified fish line in which the germ cell of a rainbow trout had been visualized with a green fluorescent protein was used, and as a result, it became possible to easily confirm the success or failure of the transplantation. In addition, in order to apply such heteroplastic germ cell transplantation to native, endangered fish species or cultured fish species, a method for confirming the success or failure of the transplantation without using a genetically modified fish line has already been developed. By this method, the present inventors have succeeded in detecting wild-type rainbow trout germ cells surviving at the genital gland of a *Salvelinus pulvius* host. The present inventors aim to apply this heteroplastic germ cell transplantation method to other marine fish species. However, to realize this object, it is essential to develop a method for confirming whether or not the transplanted germ cells of a Perciformes donor fish such as a tuna have been incorporated into the genital gland of a host and they survive therein.

In order to develop such method, the present inventors have selected Vasa gene from among Nanos gene, Deadend gene, Vasa gene, and other genes, which had been known to be specifically expressed in primordial germ cells. Thereafter, the inventors have determined for the first time the nucleotide sequences of the Vasa genes of a tuna, a chub mackerel, a spotted mackerel, an eastern little tune, and a drum fish. Further, the inventors have focused on a tuna Vasa gene, which is most likely to become a Perciformes donor fish, and they have confirmed that such tuna Vasa gene is specifically expressed in the primordial germ cell and spermatogonium/oogonium of a tuna. At the same time, in order to avoid incorrect detection of a drumfish Vasa gene having extremely high homology with the tuna Vasa gene, the inventors have specified a region characteristic for the tuna Vasa gene, and thus they have found that this region can be used as an identification marker for a spermatogonium/an oogonium derived from tuna primordial germ cells. Moreover, in order to analyze tuna germ cells transplanted into the genital gland of a host, it is essential to establish a method of distinguishing a tuna Vasa gene from a host Vasa gene and then detecting only the tuna gene. However, since the nucleotide sequences of the Vasa genes of fish species are extremely highly homologous with one another, it had been difficult to design a PCR primer set for specifically detecting the expression of a tuna Vasa gene. Thus, the inventors of the present application have carried out nested PCR that enables highly specific amplification from a trace amount of DNA, so that they could specifically detect a tuna Vasa gene. Furthermore, the inventors have compared the sequence of a tuna Vasa gene with the sequence of a Vasa gene of another Perciformes fish, and as a result, they have specified a restriction enzyme sequence existing only in the tuna Vasa gene. By combining such nested PCR with a restriction enzyme treatment, the present inventors have established a method for more reliably detecting a tuna Vasa gene, thereby completing the present invention.

Specifically, the present invention relates to
(1) a protein consisting of the amino acid sequence shown in SEQ ID NO 2 of the sequence listing; a protein, which consists of an amino acid sequence comprising a substitution, deletion, insertion, or addition of one or several amino acids with respect to the amino acid sequence shown in SEQ ID NO: 2 of the sequence listing, and which is specifically expressed in a tuna germ cell; or a protein, which consists of an amino acid sequence having homology of at least 85% or more with the amino acid sequence shown in SEQ ID NO: 2 of the sequence listing, and which is specifically expressed in a tuna germ cell,
(2) a DNA encoding a protein consisting of the amino acid sequence shown in SEQ ID NO: 2 of the sequence listing; a protein, which consists of an amino acid sequence comprising a substitution, deletion, insertion, or addition of one or several amino acids with respect to the amino acid sequence shown in SEQ ID NO: 2 of the sequence listing, and which is specifically expressed in a tuna germ cell; or a protein, which consists of an amino acid sequence having homology of at least 85% or more with the amino acid sequence shown in SEQ ID NO: 2 of the sequence listing, and which is specifically expressed in a tuna germ cell, and
(3) a DNA consisting of the nucleotide sequence shown in SEQ ID NO: 1 of the sequence listing; a DNA, which hybridizes under stringent conditions with a DNA consisting of a sequence complementary to the nucleotide sequence shown in SEQ ID NO: 1 of the sequence listing, and which encodes a protein specifically expressed in a tuna germ cell; a DNA, which hybridizes under stringent conditions with a DNA consisting of a nucleotide sequence having a function as a primer or a probe produced from a portion of the nucleotide sequence shown in SEQ ID NO: 1 of the sequence listing, and which encodes a protein specifically expressed in a tuna germ cell; or a DNA, which consists of a nucleotide sequence comprising a substitution, deletion, insertion, or addition of one or several nucleotides with respect to the nucleotide sequence shown in SEQ ID NO: 1 of the sequence listing, and which encodes a protein specifically expressed in a tuna germ cell.

In addition, the present invention relates to
(4) a protein consisting of the amino acid sequence shown in SEQ ID NO: 4, 6, 8, or 10 of the sequence listing; a protein, which consists of an amino acid sequence comprising a substitution, deletion, insertion, or addition of one or several amino acids with respect to the amino acid sequence shown in SEQ ID NO: 4, 6, 8, or 10 of the sequence listing, and which is specifically expressed in the germ cell of a Perciformes fish; or a protein, which consists of an amino acid sequence having homology of at least 85% or more with the amino acid sequence shown in SEQ ID NO: 4, 6, 8, or 10 of the sequence listing, and which is specifically expressed in the germ cell of a Perciformes fish,
(5) a DNA encoding a protein consisting of the amino acid sequence shown in SEQ ID NO: 4, 6, 8, or 10 of the sequence listing; a protein, which consists of an amino acid sequence comprising a substitution, deletion, insertion, or addition of one or several amino acids with respect to the amino acid sequence shown in SEQ ID NO: 4, 6, 8, or 10 of the sequence listing, and which is specifically expressed in the germ cell of a Perciformes fish; or a protein, which consists of an amino acid sequence having homology of at least 85% or more with the amino acid sequence shown in SEQ ID NO: 4, 6, 8, or 10 of the sequence listing, and which is specifically expressed in the germ cell of a Perciformes fish, and
(6) a DNA consisting of the nucleotide sequence shown in SEQ ID NO: 3, 5, 7, or 9 of the sequence listing; a DNA, which hybridizes under stringent conditions with a DNA consisting of a sequence complementary to the nucleotide sequence shown in SEQ ID NO: 3, 5, 7, or 9 of the sequence listing, and which encodes a protein specifically expressed in the germ cell of a Perciformes fish; a DNA, which hybridizes under stringent conditions with a DNA consisting of a nucleotide sequence having a function as a primer or a probe-produced from a portion of the nucleotide sequence shown in SEQ ID NO: 3, 5, 7, or 9 of the sequence listing, and which encodes a protein specifically expressed in the germ cell of a Perciformes fish; or a DNA, which consists of a nucleotide sequence comprising a substitution, deletion, insertion, or addition of one or several nucleotides with respect to the nucleotide sequence shown in SEQ ID NO: 3, 5, 7, or 9 of the sequence listing, and which encodes a protein specifically expressed in the germ cell of a Perciformes fish.

Moreover, the present invention relates to (7) a recombinant vector comprising the DNA according to (2), (3), (5), or (6),
(8) a transformant transformed with the recombinant vector according to (7),
(9) a fusion protein or fusion peptide, or salt thereof obtained by binding the protein according to (1) or (4) with a marker protein and/or a peptide tag,
(10) an antibody against the protein according to (1) or (4), or the fusion protein or fusion peptide according to (9), or salt thereof, and
(11) a primer set or a probe for detecting the presence of a DNA and/or mRNA encoding the protein according to (1) or (4).

Furthermore, the present invention relates to

(12) a method for detecting a primordial germ cell, a spermatogonium, or an oogonium derived from a Perciformes donor fish, which has been transplanted into a recipient fish of a different species, which methods comprises using the primer set or probe according to (11),
(13) the detection method according to (12), which comprises: treating a DNA fragment amplified by PCR using the primer set according to (11) with at least one restriction enzyme; and determining whether or not the amplified DNA fragment is derived from the Perciformes donor fish, using the length of the digested or undigested DNA fragment as an indicator,
(14) the detection method according to (12) or (13), wherein the Perciformes donor fish is a tuna,
(15) the detection method according to (14), wherein the primer set is designed to amplify a region comprising a restriction enzyme HpaI recognition sequence existing in a DNA encoding the protein according to (1); and which method comprises treating a DNA fragment amplified by PCR using the primer set with HpaI, and determining that the DNA fragment is derived from bluefin tuna DNA, when it is digested, and
(16) the detection method according to (15), wherein the PCR is nested PCR using a first primer set consisting of the nucleotide sequences shown in SEQ ID NOS: 19 and 20 and a nested primer set consisting of the nucleotide sequences shown in SEQ ID NOS: 21 and 22.

Still further, the present invention relates to

(17) a method for detecting a primordial germ cell, a spermatogonium, or an oogonium derived from a Perciformes donor fish, which has been transplanted into a recipient fish of a different species, which method comprises using the antibody according to (10),
(18) the detection method according to (17), wherein the Perciformes donor fish is a tuna,
(19) a method for evaluating the growth and/or maturation of a tuna germ cell derived from a Perciformes donor fish transplanted into a recipient fish of a different species, which comprises the detection method according to any one of (12) to (18), and
(20) the evaluation method according to (19), wherein the Perciformes donor fish is a tuna.

BRIEF DESCRIPTION OF DRAWINGS

FIG. 1 is a view showing the results obtained by staining the testis tissues of a bluefin tuna by in situ hybridization using an RNA probe specific to a bluefin tuna Vasa gene.

FIG. 2 is a view showing the results obtained by staining the testis tissues of a bluefin tuna and those of a drumfish (*Nibea mitsukurii*) by in situ hybridization using an RNA probe specific to the Vasa gene of each fish.

[FIG. 3]
FIG. 3 is a view showing sites recognized by bluefin tuna Vasa cDNA detection primers and restriction enzyme. "Bluefin tuna vasa cDNA" corresponds to the nucleotide sequence spanning nucleotide positions 1381-1859 in SEQ ID NO: 1, and "Drumfish vasa cDNA" corresponds to the nucleotide sequence spanning nucleotide positions 589-1068 in SEQ ID NO: 18, respectively.

[FIG. 4-1]
FIG. 4-1 is a view showing the results obtained by performing PCR using, as a template, a sample obtained by adding a different amount of a cDNA derived from the ovary of a bluefin tuna to a cDNA derived from the ovary of a drumfish (*Nibea mitsukurii*).

[FIG. 4-2]
FIG. 4-2 is a view showing a bluefin tuna Vasa sequence (179 bp) amplified by PCR, which is cleaved by HpaI into fragments of 146 bp and 33 bp.

FIG. 5 is a view showing the results obtained by analyzing a sample collected from the genital gland of a drumfish (*Nibea mitsukurii*).

[FIG. 6]
FIG. 6 is a view showing a comparison made among a bluefin tuna Vasa gene region amplified by the nested PCR of Example 5, and the Vasa gene regions of a drumfish (*Nibea mitsukurii*), a mackerel, and an eastern little tuna (*Euthynnus affinis*), which are highly homologous with the bluefin tuna Vasa gene region. "Bluefin" corresponds to the nucleotide sequence spanning nucleotide positions 1462-1819 in SEQ ID NO: 1, "nibe" corresponds to the nucleotide sequence spanning nucleotide positions 1418-1775 in SEQ ID NO: 9, "saba" corresponds to the nucleotide sequence shown in SEQ ID NO: 23, and "suma" corresponds to the nucleotide sequence shown in SEQ ID NO: 24, respectively.

[FIG. 7]
FIG. 7 is a view showing the results obtained by performing nested PCR using, as a template, a sample derived from the ovary of a mackerel and that of an eastern little tuna (*Euthynnus affinis*), and then treating the PCR product with HpaI.

BEST MODE OF CARRYING OUT THE INVENTION

Figure 1:
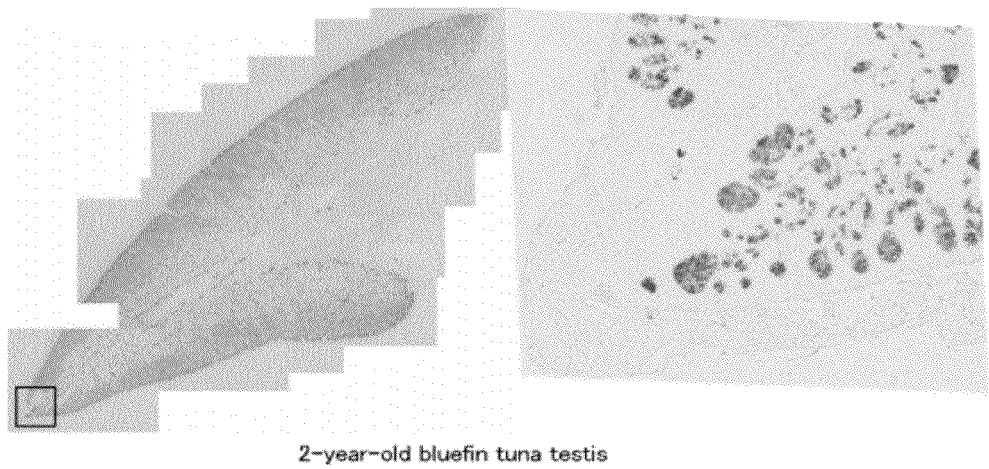
[FIG. 1]

The protein of the present invention is not particularly limited, as long as it is a protein consisting of the amino acid sequence shown in SEQ ID NO: 2 of the sequence listing (tuna Vasa protein); a protein comprising a substitution, deletion, insertion, or addition or one or several amino acids with respect to the amino acid sequence shown in SEQ ID NO: 2 and being specifically expressed in a tuna germ cell; or a protein consisting of an amino acid sequence having homology of at least 85% with the amino acid sequence shown in SEQ ID NO: 2 of the sequence listing and being specifically expressed in a tuna germ cell. In addition, the term "tuna" is used in the present invention as a generic name for fishes of Perciformes, Scombroidei, Scombridae, and Thunnus. Specific examples of such tuna include bluefin tuna, bigeye tuna, southern bluefin tuna, yellowfin tuna, albacore tuna, northern bluefin tuna, and longtail tuna. Among these, bluefin tuna is preferred. The description "protein being specifically expressed in a tuna germ cell" is used in the present invention to mean a protein, which is expressed only in a primordial germ cell, a spermatogonium, and/or an oogonium that are the germ cells of tuna, and which is not expressed in a primordial germ cell, a spermatogonium, and/or an oogonium that are the germ cells of fish species other than tuna.

In addition, the protein of the present invention is not particularly limited, as long as it is a protein consisting of the amino acid sequence shown in SEQ ID NO: 4 (chub mackerel Vasa protein), SEQ ID NO: 6 (spotted mackerel Vasa protein), SEQ ID NO: 8 (eastern little tuna (*Euthynnus affinis*) Vasa protein), or SEQ ID NO: 10 (drumfish (*Nibea mitsukurii*) Vasa protein) of the sequence listing; a protein consisting of an amino acid sequence comprising a substitution, deletion, insertion, or addition of one or several amino acids with respect to the amino acid sequence shown in SEQ ID NO: 4, 6, 8, or 10, and being specifically expressed in the germ cell of a Perciformes fish; or a protein consisting of an amino acid sequence having homology of at least 85% with the amino acid sequence shown in SEQ ID NO: 4, 6, 8, or 10 of the sequence listing, and being specifically expressed in the germ cell of a Perciformes fish. Herein Perciformes includes Percoidei, Labroidei, Zoarcoidei, Notothenioidei, Trachinoidei, Blennoidei, Gobiesocoidei, Callionymoidei, Gobioidei, Acanthuridae, Scombroidei, Stromateoidei, Anabantoidei, Channoidei, and the like. Moreover, the aforementioned chub mackerel and spotted mackerel are fishes belonging to Perciformes, Scombroidei, Scombridae, Scomber. The aforementioned eastern little tuna is a generic name for fishes belonging to Perciformes, Scombroidei, Scombridae, Euthynnus, and it includes eastern little tuna (scientific name: *Euthynnus affinis*), frigate mackerel, bullet tuna, oriental bonito, and the like. Thus, eastern little tuna used as a collective noun in the present specification is distinguished from eastern little tuna (*Euthynnus affinis*) that indicates a specific fish species, based on the presence or absence of the scientific name. The aforementioned drumfish is a generic name for fishes belonging to Perciformes, Percoidei, Sciaenidae, Nibea, and it includes drumfish (scientific name: *Nibea mitsukurii*), *Nibea albiflora*, soldier croaker, mulloway, pajama cardinalfish, drum, and the like. Thus, drumfish used as a collective noun in the present specification is distinguished from drumfish (*Nibea mitsukurii*) that indicates a specific fish species, based on the presence or absence of the scientific name. Further, such tuna, chub mackerel, spotted mackerel, and eastern little tuna are all classified into Scombroidei in Perciformes, and thus these fish species are particularly preferably used in heteroplastic transplantation.

The above description "an amino acid sequence comprising a substitution, deletion, insertion, or addition of one or several amino acids" means an amino acid sequence comprising a substitution, deletion, insertion, or addition of any given number of, for example 1 to 20, preferably 1 to 15, more preferably 1 to 10, and further preferably 1 to 5 amino acids. In addition, the above-described "an amino acid sequence having homology of at least 85% with the amino acid sequence shown in SEQ ID NO: 2, 4, 6, 8, or 10" is not particularly limited, as long as it has homology of 85% or more with the amino acid sequence shown in SEQ ID NO: 2, 4, 6, 8, or 10. Thus, such homology is, for example, 85% or more, preferably 90% or more, more preferably 95% or more, and particularly preferably 98% or more.

A method of obtaining or preparing the protein of the present invention is not particularly limited. Any one of an isolated, naturally-derived protein, a chemically synthesized protein, and a recombinant protein produced by a genetic recombination technique may be used. In the case of obtaining a naturally-derived protein, the protein of the present invention can be obtained from cells that express such protein by appropriately combining methods of isolating and purifying protein.

In the case of preparing the protein of the present invention by chemical synthesis, chemical synthesis methods such as an Fmoc method protein (fluorenylmethyloxycarbonyl method) or a tBoc method (t-butyloxycarbonyl method) are applied to obtain the protein of the present invention. Moreover, the protein of the present invention can also be synthesized based on the amino acid sequence information, using various types of commercially available peptide synthesizers.

In the case of preparing the protein of the present invention by a genetic recombination technique, a DNA encoding the protein is introduced into a preferred expression system, so as to prepare the protein of the present invention. Among these protein preparation methods, a genetic recombination technique that is capable of prepare a large amount of protein by comparatively easily operations is preferred.

When the protein of the present invention is prepared by such genetic recombination technique, in order to recover and purify the protein from a cell culture, precipitation with ammonium sulfate or ethanol and acid extraction are carried out, and thereafter, known methods including anion or cation exchange chromatography, phosphocellulose chromatography, hydrophobic interaction chromatography, affinity chromatography, hydroxyapatite chromatography, and lectin chromatography are used. Preferably, high performance liquid chromatography is used.

In particular, as a column used in affinity chromatography, for example, a column to which an antibody such as a monoclonal antibody against the protein of the present invention is allowed to bind, or in a case in which an ordinary peptide tag is added to the aforementioned protein of the present invention, a column to which a substance having affinity for the peptide tag is allowed to bind, is used to obtain a purified product of such protein. In addition, the protein of the present invention prepared by the aforementioned methods can be used in a method for specifically detecting a primordial germ cell, a spermatogonium, and/or an oogonium derived from Perciformes.

Furthermore, a person skilled in the art could appropriately prepare or obtain a protein consisting of an amino acid sequence comprising a substitution, deletion, insertion, or addition of one or several amino acids with respect to the amino acid sequence shown in SEQ ID NO: 2, 4, 6, 8, or 10, or a protein consisting of an amino acid sequence having homology of at least 85% with the amino acid sequence shown in SEQ ID NO: 2, 4, 6, 8, or 10 of the sequence listing, based on information regarding the nucleotide sequence shown in SEQ ID NO: 1, 3, 5, 7, or 9 of the sequence listing, which is given as an example of a nucleotide sequence encoding, respectively, the amino acid sequence shown in SEQ ID NO: 2, 4, 6, 8, or 10. For example, by a polymerase chain reaction (PCR reaction) using, as primers, oligonucleotides synthesized based on the nucleotide sequence shown in SEQ ID NO: 1, 3, 5, 7, or 9, or by hybridization using, as a probe, an oligonucleotide synthesized based on the same above nucleotide sequence, DNA homologs from tuna species other than bluefin tuna are screened under appropriate conditions, so as to isolate them. The entire-length DNA of this homolog DNA is cloned, incorporated into an expression vector, and then allowed to express in a suitable host, so that a protein encoded by the homolog DNA can be produced.

An oligonucleotide can be synthesized according to an ordinary method, for example, using various commonly available DNA synthesizers. In addition, a PCR reaction can be carried out according to an ordinary method employing the Gene Amp PCR system 2400 Thermal Cycler manufactured by Applied Biosystems, and using Taq DNA polymerase (manufactured by Takara Bio Inc.) or KOD-Plus-(manufactured by Toyobo Co., Ltd.).

Moreover, the aforementioned protein of the present invention may be allowed to bind to a marker protein and/or a peptide tag to produce a fusion protein. The type of a marker protein is not particularly limited, as long as it is a conventionally known marker protein. Specific examples of such marker protein include luciferase, alkaline phosphatase, enzyme such as HRP, an antibody Fc region, and fluorescent substances such as GFP, YFP, CFP, DsRed and aequorin. Specific examples of such peptide tag include conventionally known peptide tags including epitope tags such as HA, FLAG and Myc, affinity tags such as GST, a maltose binding protein, a biotinylated peptide and oligohistidine. Such fusion protein can be produced by an ordinary method, and it is useful for purification of the protein of the present invention using the affinity of Ni-NTA with a His tag, detection of the protein of the present invention, or quantification of an antibody against the protein of the present invention, and is also useful as a reagent for studies in the present field.

Next, the DNA of the present invention is not particularly limited, as long as it is a DNA encoding a protein consisting of the amino acid sequence shown in SEQ ID NO: 2; a DNA encoding a protein, which consists of an amino acid sequence comprising a substitution, deletion, insertion, or addition of one or several amino acids with respect to the amino acid sequence shown in SEQ ID NO: 2, and which is specifically expressed in a tuna germ cell; a DNA encoding a protein, which consists of an amino acid sequence having homology of at least 85% with the amino acid sequence shown in SEQ ID NO: 2, and which is specifically expressed in a tuna germ cell; a DNA consisting of the nucleotide sequence shown in SEQ ID NO: 1 (a bluefin tuna Vasa gene); a DNA, which hybridizes under stringent conditions with a DNA consisting of a sequence complementary to the nucleotide sequence shown in SEQ ID NO: 1, and which encodes a protein specifically expressed in a tuna germ cell; a DNA, which hybridizes under stringent conditions with a DNA consisting of a nucleotide sequence having a function as a primer or a probe produced from a portion of the nucleotide sequence shown in SEQ ID NO: 1 of the sequence listing, and which encodes a protein specifically expressed in a tuna germ cell; or a DNA, which consists of a nucleotide sequence comprising a substitution, deletion, insertion, or addition of one or several nucleotides with respect to the nucleotide sequence shown in SEQ ID NO: 1, and which encodes a protein specifically expressed in a tuna germ cell. The above description "a nucleotide sequence comprising a substitution, deletion, insertion, or addition of one or several nucleotides" means a nucleotide sequence comprising a substitution, deletion, insertion, or addition of any given number of, for example 1 to 20, preferably 1 to 15, more preferably 1 to 10, and further preferably 1 to 5 nucleotides.

Hence, the DNA of the present invention encoding a protein that is specifically expressed in a tuna germ cell may encode a protein comprising a deletion, substitution, insertion, or addition of one or several amino acids at one or several positions, unless it impairs the function of a tuna Vasa protein. Such DNA encoding a protein that is specifically expressed in a tuna germ cell can also be obtained by subjecting nucleotide(s) at specific site(s) to a deletion, substitution, insertion, or addition of nucleotide(s), so as to modify the nucleotide sequence, for example, by site-directed mutagenesis. In addition, the above modified DNA can also be obtained by conventionally known mutagenesis. Moreover, it has been generally known that the amino acid sequences of proteins and nucleotides sequences encoding them are slightly different among species. Thus, it is possible to obtain a DNA encoding a protein specifically expressed in a bluefin tuna germ cell from tuna species other than the bluefin tuna.

Furthermore, the DNA of the present invention is not particularly limited, as long as it is a DNA encoding a protein consisting of the amino acid sequence shown in SEQ ID NO: 4, 6, 8, or 10; a DNA encoding a protein, which consists of an amino acid sequence comprising a substitution, deletion, insertion, or addition of one or several amino acids with respect to the amino acid sequence shown in SEQ ID NO: 4, 6, 8, or 10, and which is specifically expressed in the germ cell of a Perciformes fish; a DNA encoding a protein, which consists of an amino acid sequence having homology of at least 85% with the amino acid sequence shown in SEQ ID NO: 4, 6, 8, or 10, and which is specifically expressed in the germ cell of a Perciformes fish; a DNA consisting of the nucleotide sequence shown in SEQ ID NO: 3 (chub mackerel Vasa gene), NO: 5 (spotted mackerel Vasa gene), NO: 7 (eastern little tuna (*Euthynnus affinis*) Vasa gene), or NO: 9 (drumfish (*Nibea mitsukurii*) Vasa gene); a DNA, which hybridizes under stringent conditions with a DNA consisting of a sequence complementary to the nucleotide sequence shown in SEQ ID NO: 3, 5, 7, or 10, and which encodes a protein specifically expressed in the germ cell of a Perciformes fish; a DNA, which hybridizes under stringent conditions with a DNA consisting of a nucleotide sequence having a function as a primer or a probe produced from a portion of the nucleotide sequence shown in SEQ ID NO: 3, 5, 7, or 9, and which encodes a protein specifically expressed in the germ cell of a Perciformes fish; or a DNA, which consists of a nucleotide sequence comprising a substitution, deletion, insertion, or addition of one or several amino acids with respect to the nucleotide sequence shown in SEQ ID NO: 3, 5, 7, or 9, and which encodes a protein specifically expressed in the germ cell of a Perciformes fish. The above description "a nucleotide sequence comprising a substitution, deletion, insertion, or addition of one or several nucleotides" means a nucleotide sequence comprising a substitution, deletion, insertion, or addition of any given number of, for example 1 to 20, preferably 1 to 15, more preferably 1 to 10, and further preferably 1 to 5 nucleotides.

The DNA of the present invention encoding a protein specifically expressed in the germ cell of a Perciformes fish may encode a protein comprising a deletion, substitution, insertion, or addition of one or several amino acids at one or several positions, unless it impairs the function of a Vasa protein. Such DNA encoding a protein that is specifically expressed in the germ cell of a Perciformes fish can also be obtained by subjecting nucleotide(s) at specific site(s) to a deletion, substitution, insertion, or addition of nucleotide(s), so as to modify the nucleotide sequence, for example, by site-directed mutagenesis. In addition, the above modified DNA can also be obtained by conventionally known mutagenesis.

For instance, as stated above, a DNA consisting of a nucleotide sequence comprising a substitution, deletion, insertion, or addition of one or several nucleotides (mutant DNA) can also be produced by any given methods known to persons skilled in the art, such as chemical synthesis, a genetic engineering method, or mutagenesis. Specifically, a mutation is introduced into a DNA consisting of the nucleotide sequence shown in SEQ ID NO: 1 by a method of allowing an agent acting as a mutagen to come into contact with and act on the DNA, a method of applying ultraviolet ray to the DNA, a genetically engineering method, or the like, thereby obtaining a mutant DNA. Site-directed mutagenesis used as a genetically engineering method is a useful method capable of introducing a specific mutation into a specific site, and this method is carried out according to the methods described in Molecular Cloning: A laboratory Manual, 2nd Ed., Cold Spring Harbor Laboratory, Cold Spring Harbor, N.Y., 1989; Current Protocols in Molecular Biology, Supplement 1-38, John Wiley & Sons (1987-1997); etc. By allowing this mutant DNA to express in a suitable expression system, a protein consisting of an amino acid sequence comprising a substitution, deletion, insertion, or addition of one or several amino acids can be obtained.

The aforementioned description "under stringent conditions" is used to mean conditions under which a so-called specific hybrid is formed and a non-specific hybrid is not formed. Specific examples of such stringent conditions include: conditions under which DNA portions having homology of 50% or more, and preferably 70% or more hybridize with each other and DNA portions having homology lower than that as described above do not hybridize with each other; and washing conditions in ordinary Southern hybridization, under which hybridization is carried out at 65° C. in a salt concentration corresponding to a 1×SSC solution (wherein the composition of a 1-fold concentration of SSC solution consists of 150 mM sodium chloride and 15 mM sodium citrate) and 0.1% SDS, or 0.1×SSC and 0.1 SDS.

In addition, the above description "DNA, which hybridizes under stringent conditions" is used to mean a DNA obtained by applying a colony hybridization method, a plaque hybridization method, a Southern blot hybridization, or the like, using a nucleic acid such as DNA or RNA as a probe. A specific example of such DNA is a DNA, which can be identified by carrying out hybridization at 65° C. in the presence of 0.7 to 1.0 M NaCl using a filter, on which a colony- or plaque-derived DNA or a fragment thereof has been immobilized, and then by washing the filter at 65° C. using an approximately 0.1 to 2×SSC solution.

Hybridization can be carried out according to the method described in Molecular Cloning, 2nd Ed. An example of a DNA capable of hybridizing with another DNA under stringent conditions is a DNA having a certain level of homology with the nucleotide sequence of a DNA used as a probe. A preferred example of such DNA is a DNA having homology of, for example, 60% or more, preferably 70% or more, more preferably 80% or more, further preferably 90% or more, particularly preferably 95% or more, and most preferably 98% or more, with another DNA.

A method of obtaining or preparing a DNA of the present invention is not particularly limited. An appropriate probe or primer is prepared based on the information of the nucleotide sequence shown in SEQ ID NO: 1 or the information of the amino acid sequence shown in SEQ ID NO: 2 disclosed in the present specification. Thereafter, using such probe or primer, a cDNA library in which the DNA is estimated to exist is screened to isolate the DNA of interest. Alternatively, such DNA can also be prepared by carrying out chemical synthesis according to an ordinary method.

For example, a cDNA library is prepared from tuna according to an ordinary method, and thereafter, a desired clone is selected from this library using an appropriate probe specific to the genetic DNA of the present invention, so as to obtain the genetic DNA of the present invention. Moreover, separation of total RNA from tuna, separation and purification of mRNA, the obtainment of cDNA, and the cloning thereof can all be carried out according to ordinary methods. Examples of a method of screening the genetic DNA of the present invention from a cDNA library include methods commonly used by persons skilled in the art, such as the method described in Molecular Cloning, 2nd Ed.

The recombinant vector of the present invention is not particularly limited, as long as it comprises the aforementioned gene of the present invention and is able to express a protein specific to the germ cell of a Perciformes fish. The recombinant vector of the present invention can be constructed by appropriately integrating the DNA of the present invention into an expression vector used for animal cells or an expression vector used for microorganisms. As such expression vector, an expression vector capable of autonomously replicating in a host cell or an expression vector capable of being incorporated into the chromosome of a host cell is preferred. In addition, an expression vector comprising control sequences such as a promoter, an enhancer, and a terminator at positions that enable the expression of the DNA of the present invention, can preferably be used. Moreover, the DNA of the present invention produced by the aforementioned method can be used for a method for specifically detecting a primordial germ cell, a spermatogonium, and/or an oogonium derived from Perciformes.

Furthermore, the recombinant vector of the present invention can also be used to produce a transformant. For transformation, commonly used transformation methods can all be applied. For example, a vector is packaged in a retrovirus particle or a lambda virus particle, and it is then transferred into a cell. Otherwise, by applying microinjection, electroporation, calcium phosphate precipitation, or a biolistic method (for example, tungsten bombardment), or by allowing a naked nucleic acid vector or construct to come into contact with a cell in a solution, such vector can be introduced into a cell. Among these methods, introduction by microinjection is particularly preferred. Such microinjection can be carried out before or after fertilization, or at the two-celled, four-celled or eight-celled stage after cleavage. The obtained cells are cultured by an ordinary method, so that they are allowed to grow to an embryo, a baby fish, a juvenile fish, a young fish, and a mature fish, which have germ cells.

Examples of an antibody of the present invention include a monoclonal antibody, a polyclonal antibody, a single-stranded antibody, a humanized antibody, a chimeric antibody, and a bifunctional antibody capable of simultaneously recognizing two epitopes. These antibodies are produced by administering a fragment containing the protein of the present invention or an epitope, an analog, or the like to animals (preferably, animals other than a human) in accordance with commonly used protocols. For example, in order to prepare a monoclonal antibody, there can be used any given methods such as a hybridoma method (Nature 256, 495-497, 1975), a trioma method, a human B cell hybridoma method (Immunology Today 4, 72, 1983), and an EBV-hybridoma method (MONOCLONAL ANTIBODIES AND CANCER THERAPY, pp. 77-96, Alan R. Liss, Inc., 1985), which bring on antibodies produced from a culture product of a continuous cell line. Moreover, an Fab fragment or an F(ab')2 fragment of the aforementioned antibodies, and the like, may also be used similarly as the aforementioned antibodies. As an antigen, a peptide consisting of 4 or more, preferably 6 or more, and more preferably 10 or more amino acids, encoded by the Vasa gene of the present invention, may be synthesized and used. Or, there may be used a product obtained by allowing a part of or the entire Vasa gene of the present invention to express in the cell of phage, *Escherichia coli*, Actinomycetes, lactic acid bacteria, yeast, a cultured cell, or the like. Otherwise, the entire or a part of a Vasa gene product may be purified from a fish individual or cell thereof, and it may be then used. In the production of the aforementioned antigen, in order to produce an antibody specifically recognizing the Vasa gene product of a Perciformes fish as a target, it is preferred to select a gene region encoding an amino acid sequence specific to the Perciformes fish species as a target from the amino acid sequence of a Vasa protein. In immunization with the aforementioned antigen, the antigen may be directly used. Otherwise, the antigen may be mixed with or bind to an immunopotentiating agent or adjuvant such as hapten, and it may be then used.

Labeled antibodies produced by labeling the aforementioned antibodies, for example, with fluorescent substances such as FITC (fluorescein isocyanate) or tetramethylrhodamine isocyanate, with radioisotopes such as 125I, 32P, 14C, 35S or 3H, or with enzymes such as alkaline phosphatase, peroxidase, β-galactosidase or phycoerythrin, or fusion proteins produced by fusing such antibodies with fluorescent proteins such as green fluorescent protein (GFP), can be used to detect and measure the protein of the present invention by an immunological method. Examples of such immunological method include an RIA method, an ELISA method, a fluorescent antibody method, a plaque method, a spot method, an erythrocyte agglutination reaction method, and an Ouchterlony method.

Further, the present invention relates to a primer set for detecting the presence of a DNA and/or mRNA encoding the Vasa protein of the present invention that is specifically expressed in a germ cell. For example, with regard to a primer set for detecting the presence of a DNA or mRNA encoding a protein specifically expressed in a tuna germ cell, the length of the primer sequence, the site of the nucleotide sequence of a nucleic acid to which the primer set is complementary, and the like are not particularly limited, as long as it is a complementary primer set capable of hybridizing with a portion of a sequence upstream or downstream of the DNA, mRNA, or cDNA of the protein. For example, even if such primers comprise a sequence wherein a part is not complementary to the DNA, mRNA, or cDNA sequence of the aforementioned peptide on the 5'- or 3'-terminal side or on both sides, as far as they are able to hybridize with them, they can be used as primers. Moreover, in order to prevent non-specific amplification or to introduce a suitable restriction enzyme recognition site, it is possible to use a primer having a mismatch sequence that is not complementary to such DNA, mRNA, or cDNA.

Furthermore, the present invention relates to a probe for detecting the presence of a DNA and/or mRNA encoding the protein of the present invention that is specifically expressed in a germ cell. A preferred example of a probe for detecting the presence of a DNA or mRNA encoding a protein specifically expressed in a tuna germ cell is a probe, which is the entire or a part of antisense strand capable of hybridizing with a DNA (cDNA) or RNA (cRNA) encoding such peptide, and which has a length necessary as a probe (at least 20 bases or more). For example, even if such probe comprises a sequence wherein a part is not complementary to the DNA, mRNA, or cDNA sequence of the aforementioned peptide on the 5'- or 3'-terminal side or on both sides, as far as the probe is able to hybridize with them, it can be used as a probe. Further, for easy detection, a probe to which any given sequence has been added can be used. Still further, for easy detection, a probe whose 5'-terminus has been labeled can also be used. Examples of a labeling substance used herein include biotin, fluorescence, and P32.

The method of the present invention for identifying a primordial germ cell, a spermatogonium, or an oogonium derived from a donor fish is not particularly limited, as long as it is a method by which the presence of a DNA and/or mRNA encoding a protein specifically expressed in a tuna germ cell in a sample is detected by an in situ hybridization method or the like using the aforementioned primer set or labeled probe of the present invention, and when the presence of such DNA and/or mRNA is detected in the sample, it is evaluated that a primordial germ cell, a spermatogonium, or an oogonium derived from a tuna is present in the sample. As a particularly simple, highly accurate identification method, there may be a method of treating a DNA fragment amplified by PCR using the aforementioned primer set of the present invention with at least one restriction enzyme and then using the length of the treated DNA fragment as an indicator. The restriction enzyme used in the aforementioned method is not particularly limited, as long as it is used to obtain DNA fragments with different lengths between a DNA derived from a donor fish and a DNA derived from a recipient fish of a different species, such as restriction enzyme whose recognition sequence exists in a donor fish Vasa gene region to be amplified but does not exist in a different species of recipient fish Vasa gene region, restriction enzyme whose recognition sequence does not exist in a donor fish Vasa gene region to be amplified but exists in a different species of recipient fish Vasa gene region, and restriction enzyme whose recognition sequence exists both in a donor fish Vasa gene region to be amplified and in a different species of recipient fish Vasa gene region, but which number of such recognition sequences is different. As a preferred example, when a tuna is selected as a donor fish and a drumfish, and a mackerel or an eastern little tuna is selected as a recipient fish of a different species, HapI can be exemplified. An example of an identification method using the aforementioned HapI is a method, which comprises performing nested PCR using a first primer set consisting of the nucleotide sequences shown in SEQ ID NOS: 19 and 20 and a nested primer set consisting of the nucleotide sequences shown in SEQ ID NOS; 21 and 22, then treating the obtained PCR product with the restriction enzyme HapI, and then determining that the above PCR product is a tuna Vasa gene, when the PCR product is digested to DNA fragments of 146 bp and 33 bp.

The identification method of the present invention is useful as a method for evaluating the growth and/or maturation of a germ cell derived from a donor fish transplanted into a recipient fish of a different species. For example, a primordial germ cell separated from a tuna is transplanted into the early embryo of a recipient fish of a different species such as a drumfish, a mackerel, an eastern little tuna or a *Pagrus major*, which seeding production can be conducted more simply with higher efficiency than a tuna, and preferably, such primordial germ cell is transplanted into the abdominal cavity of a recipient fish of a different species at the early developing stage, so that the aforementioned primordial germ cell can be induced to differentiate into a germ cell line. Thus, in a recipient fish of a different species, a tuna-derived primordial germ cell is induced to differentiate into an oocyte or a spermatogonium, and is further induced to differentiate into an ovary or a sperm, thereby enabling the growth and breeding of tuna.

The present invention will be more specifically described in the following examples. However, these exemplifications are not intended to limit the technical scope of the present invention.

EXAMPLE 1

RNA Extraction from Bluefin Tuna Testis Tissues and cDNA Synthesis

The testis was excised from each of five cultivated male bluefin tuna fishes (3-year-old; body weight: approximately 50 kg), which was then frozen rapidly on dry ice. Total RNA was extracted from the obtained testis tissues using ISOGEN (manufactured by Nippon Gene Co., Ltd.). In order to decompose DNA, a 40 mM Tris-HCl (pH 7.8) solution containing 2.2 U/ml RQ1 RNasa-Free DNase (manufactured by Promega), RNase inhibitor (manufactured by Toyobo Co., Ltd.), 10 mM NaCl, 6 mM MgCl2, and 10 mM Dithiothreitol (DTT) was added, and the obtained mixture was then incubated at 37° C. for 60 minutes. Thereafter, phenol/chloroform extraction and ethanol precipitation were performed on the reaction solution, so as to purify total RNA, and the concentration and purity thereof were then measured. Using 2 µg of the thus extracted total RNA as a template, and employing a single-stranded cDNA synthesis kit, Ready-To-Go You-Prime First-Strand Beads (manufactured by GE Healthcare Biosciences), cDNA was synthesized.

EXAMPLE 2

Determination of Bluefin Tuna Vasa Gene Sequence

Subsequently, a comparison was made among the amino acid sequences of the Vasa proteins of previously reported fish species (rainbow trout, zebrafish, *Oryzias latipes*, gilthead, Pejerrey, tilapia, goldfish, and carp). From these sequences, regions that were expected to have high homology and to be conserved in the bluefin tuna Vasa protein were selected, and degenerate primers shown in SEQ ID NOS: 11 and 12 were then produced. Using these primers, a PCR reaction was carried out using the cDNA synthesized in Example 1 as a template, so as to amplify a DNA fragment that was estimated to be derived from the bluefin tuna Vasa gene. The nucleotide sequence of the obtained DNA fragment was determined using ABI Prism 3100-Avant Genetic Analyzer (manufactured by Applied Biosystems).

Based on the determined nucleotide sequence, a 5'-RACE primer as shown in SEQ ID NO: 13 and a 3'-RACE primer as shown in SEQ ID NO: 14 were designed. Using these primers, a RACE-PCR reaction was carried out employing GeneRacer™ KIT (Invitrogen), so as to amplify the 5'-terminal side sequence and 3'-terminal side sequence of the bluefin tuna Vasa gene. The nucleotide sequences of the 5'- and 3'-terminal sides were determined, and they were then ligated to the aforementioned nucleotide sequence to obtain the nucleotide sequence of an entire-length bluefin tuna Vasa gene. With regard to the 5'-terminus, the cDNA of bluefin tuna Vasa used as a template had a hairpin structure, and thus it was impossible to amplify the sequence up to its 5'-terminus only with a 5'-RACE primer A. Accordingly, a 5'-RACE primer B as shown in SEQ ID NO: 15 was newly designed from a nucleotide sequence determined by a RACE-PCR reaction using the 5'-RACE primer A, and a RACE-PCR reaction was carried out again to amplify a DNA fragment at the 5'-terminus, so as to determine an entire-length bluefin tuna Vasa nucleotide sequence as shown in SEQ ID NO: 1 and a bluefin tuna Vasa amino acid sequence as shown in SEQ ID NO: 2. Applying the same method, the Vasa gene of chub mackerel (SEQ ID NO: 3), the Vasa gene of spotted mackerel (SEQ ID NO: 5), the Vasa gene of eastern little tuna (*Euthynnus affinis*) (SEQ ID NO: 7), and the Vasa gene of drumfish (*Nibea mitsukurii*) (SEQ ID NO: 9) were each determined. Thereafter, amino acid sequences (SEQ ID NOS: 4, 6, 8, and 10) corresponding to these gene sequences were determined.

EXAMPLE 3

Production of RNA Probe

First, using the cDNA synthesized in Example 1 as a template, a PCR reaction was carried out with the primer shown in SEQ ID NO: 15 and the primer shown in SEQ ID NO: 16, so as to amplify a bluefin tuna Vasa fragment of 1090 by as shown in SEQ ID NO: 17. The obtained DNA fragment was inserted into a pGEM-T easy vector (manufactured by Promega), and it was then subcloned. With the produced vector as a template, an in vitro transcription reaction was carried out using digoxigenin (DIG)-labeled uridine triphosphate (DIG-11-UTP; manufactured by Roche) and RNA polymerase (SP6 or T7 RNA polymerase; manufactured by Promega), so as to synthesize sense-strand and antisense-strand RNA probes.

EXAMPLE 4

In Situ Hybridization

A 5-µm section was prepared from bluefin tuna testis tissues fixed with a Bouin's fluid, and it was then developed on a slide glass to produce a tissue section sample. A hybridization reaction solution (a 5×SSC solution (pH 4.5) containing 50 µg/ml tRNA, 50% formaldehyde, 50 µg/ml heparin, and 1% SDS) containing 1 µg/ml RNA probe produced in Example 3 was placed on the section, and it was then reacted at 65° C. for 18 hours. Thereafter, the reaction product was washed with a 1×SSC solution containing 50% formamide, and then substituted with a 1×TBST solution. Thereafter, the reaction solution was incubated with a blocking solution for hybridization (manufactured by Roche) for 1 hour.

Subsequently, signal amplification was carried out using TSA™ PlusDNP AP System (PerkinElmer Japan). Such signal amplification comprises a step of incubating the section sample obtained after blocking with horseradish peroxidase-labeled anti-DIG, Fab fragments (Anti-DIG-POD, Fab fragments: manufactured by Roche) for 30 minutes; and a step of adding dinitrophenyl (DNP)-labeled tyramide dropwise to the slide glass. Thereafter, the resultant was incubated with an alkaline phosphatase (AP)-labeled-anti-DNP antibody for 30 minutes. After the antibody solution has been washed, a color development reaction was carried out using an NBT/BCIP solution (4-nitroblue tetrazolium/5-bromo-4-chloro-3-indolyl phosphate solution; manufactured by Roche) that was a coloring substrate of AP. Finally, counter staining was carried out using Nuclear Fsat Red (manufactured by Vector Laboratories), followed by mounting with a mounting agent, Entellan New (manufactured by Merck).

Further, in the present experiment, an RNA probe specifically hybridizing with a drumfish (*Nibea mitsukurii*) Vasa gene and a drumfish (*Nibea mitsukurii*) testis tissue section were produced, and they were then used as negative controls. Such RNA probe was produced by inserting the gene sequence specific to drumfish (*Nibea mitsukurii*) shown in SEQ ID NO: 18 into a pGEM-T easy vector (manufactured by Promega) and then performing an in vitro transcription reaction by the same method as that of Example 3 using the gene sequence as a template. In addition, a drumfish (*Nibea mitsukurii*) testis tissue section sample was produced according to the method of Example 4, and in situ hybridization was then carried out.

Figure 2:
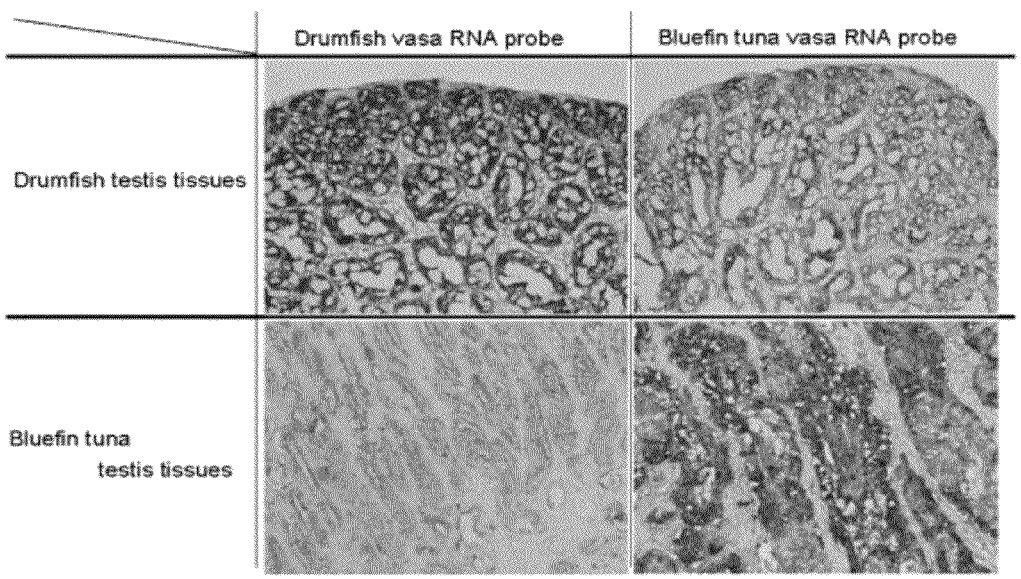
[FIG. 2]

As a result of the in situ hybridization, as shown in FIG. 1, a signal specific to spermatogonium was detected in the testis of a 2 year-old bluefin tuna. Moreover, as shown in FIG. 2, no significant signal of the bluefin tuna Vasa RNA probe was observed in the testis tissues of the drumfish (*Nibea mitsukurii*) used as a negative control. Thus, it is considered that the RNA probe produced in the present experiment specifically hybridizes with bluefin tuna Vasa. Furthermore, as a result of the experiment using a drumfish (*Nibea mitsukurii*) Vasa RNA probe, a strong signal was detected in the testis tissues of a drumfish (*Nibea mitsukurii*), whereas no significant signal was observed in the testis of a bluefin tuna (FIG. 2). These results strongly suggested that an RNA probe designed based on the bluefin tuna Vasa sequence is likely to be useful for specific detection of a bluefin tuna germ cell. Likewise, the results strongly suggested that an RNA probe designed based on the drumfish (*Nibea mitsukurii*) Vasa sequence is likely to be useful for specific detection of a drumfish (*Nibea mitsukurii*) germ cell.

EXAMPLE 5

Establishment of Method for Detecting Bluefin Tuna Germ Cell-Derived Vasa Gene

In order to detect the presence of a bluefin tuna germ cell transplanted into the genital gland of a drumfish (*Nibea mitsukurii*), there was established a simple method for detecting a bluefin tuna Vasa gene with high accuracy, in which nested PCR capable of highly specific amplification from a trace amount of DNA is combined with a treatment with restriction enzyme. FIG. 3 shows the Vasa gene regions of drumfish (*Nibea mitsukurii*) having high homology with the bluefin tuna Vasa gene sequence, and the positions of primers and restriction enzyme HpaI recognition sites, which were used in the experiment.

(1) Preparation of a Sample

A 2 mm-square ovary section was collected from the immature ovary of a bluefin tuna or a drumfish (*Nibea mitsukurii*), and the collected section was then cut into fragments with dissecting scissors. Thereafter, the cells were dispersed by treatment with trypsin. With regard to the obtained two types of cell suspensions, cell density was measured using a blood cell counter. Thereafter, each suspension was adjusted to have a cell number of interest, and the two suspensions were then mixed. In addition, when a sample in which $10^1$ tuna ovary cells were mixed with $10^6$ drumfish (*Nibea mitsukurii*) ovary cells was prepared, in order to collect an exact number of bluefin tuna ovary cells, cells were sorted under a stereoscopic microscope, using a microinjector equipped with a glass microcapillary.

Figures 2, 4:
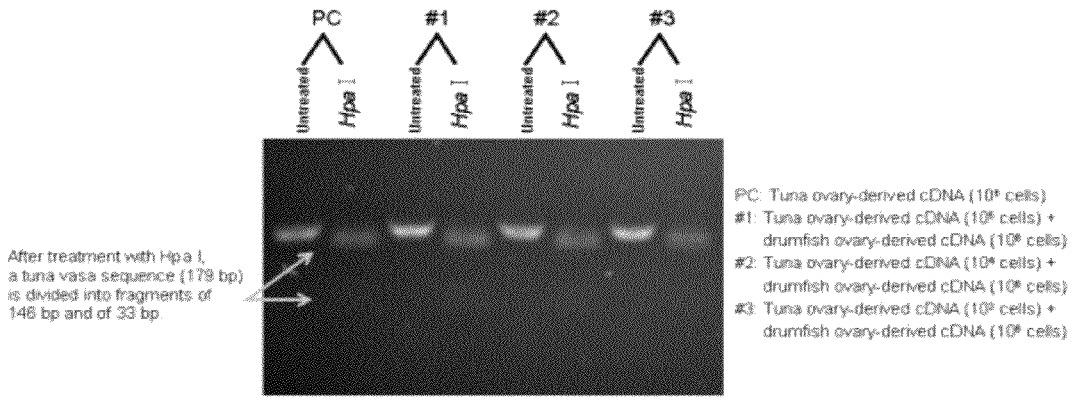
Figure 5:
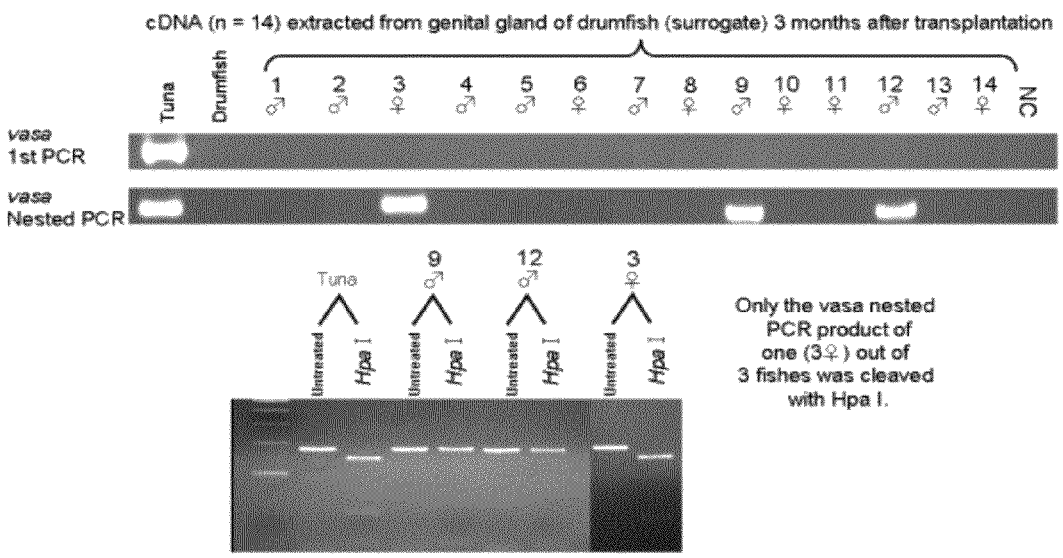
[FIG. 5]

(2) Nested PCR tRNA was extracted from cells in the prepared mixed solution using QuickPrep Total RNA Extraction Kit (manufactured by GE Healthcare), and cDNA was then synthesized using SuperScriptIII RNaseH Reverse Transcriptase (manufactured by Invitrogen). Nested PCR was carried out using a first primer set consisting of the nucleotide sequences shown in SEQ ID NOS: 19 and 20 and a nested primer set consisting of the nucleotide sequences shown in SEQ ID NOS: 21 and 22. A PCR reaction solution was prepared using TakaraExtaq (manufactured by Takara) in accordance with the protocols attached to the reagent. PCR reaction conditions consisted of: heat denaturation at 94° C. for 2 minutes; heat denaturation at 94° C. for 30 seconds, annealing at 60° C. for 30 seconds, and elongation reaction at 72° C. for 30 seconds; and elongation reaction at 72° C. for 3 minutes. As shown in FIG. 4-1, as a result of the nested PCR, a strong signal was detected in a sample containing cDNA derived from tuna ovary ($10^3$ to $10^6$ cells). In contrast, in the case of cDNA derived from only drumfish (*Nibea mitsukurii*) ovary or cDNA derived from bluefin tuna ovary ($10^2$ cells), no significant signal was detected as a result of the nested PCR. These results strongly suggested that the bluefin tuna Vasa gene was specifically amplified by the nested PCR of the present example.

(3) Restriction Enzyme HpaI Treatment

Subsequently, in order to confirm that the amplified gene fragment was not derived from the drumfish (*Nibea mitsukurii*) used as a host, but was derived from the bluefin tuna, the PCR product was digested with restriction enzyme. Since the Vasa gene sequence of bluefin tuna is extremely highly homologous with that of drumfish (*Nibea mitsukurii*), it is highly likely that the two types of genes are both amplified by nested PCR. However, as shown in FIG. 3, an HpaI recognition sequence existing in the sequence of the bluefin tuna does not exist in the drumfish (*Nibea mitsukurii*). Thus, by detecting digestion with the restriction enzyme HpaI, it is possible to determine whether the amplified PCR product was derived from the bluefin tuna or from the drumfish (*Nibea mitsukurii*). An experiment was actually carried out, and as a result, the Vasa gene sequence (179 bp) amplified by nested PCR was divided into fragments of 146 bp and 33 bp by digestion with HpaI (FIG. 4-2).

EXAMPLE 6

The sequence of the PCR product of the digested sample was confirmed. As a result, it became clear that this sequence corresponded to the sequence of bluefin tuna. These results demonstrated that the detection method in which the nested PCR is combined with the HpaI treatment is an excellent method for specifically detecting a bluefin tuna Vasa gene with no need for sequence analysis, and that a bluefin tuna germ cell that has been mixed with a drumfish (*Nibea mitsukurii*) genital gland can be simply detected by applying this detection method.

EXAMPLE 7

Furthermore, mackerel and eastern little tuna, which may be considered to be used as surrogate fish for bluefin tuna, were also analyzed. As shown in FIG. 6, the Vasa gene sequences of bluefin tuna, drumfish (*Nibea mitsukurii*), mackerel, and eastern little tuna (*Euthynnus affinis*) show high homology with one another. However, among these sequences, a sequence having an HpaI recognition sequence is only that of bluefin tuna. Nested PCR was carried out in the same manner as Example 5. As a result, strong signals were obtained from both mackerel and eastern little tuna (*Euthynnus affinis*). The PCR products were treated with HpaI. As a result, the gene fragments of mackerel and eastern little tuna were not digested, and only the gene fragment of bluefin tuna was digested (FIG. 7). These results suggest that the detection method in which the nested PCR is combined with the HpaI treatment can be applied as a method for detecting a bluefin tuna germ cell in a case in which not only drumfish (*Nibea mitsukurii*), but also mackerel or eastern little tuna (*Euthynnus affinis*), is used as surrogate fish.

INDUSTRIAL APPLICABILITY

In order to examine whether or not a germ cell derived from a donor fish, which has been transplanted into a recipient fish of a different species by a surrogate fish technique, grows or matures in the gonad of the recipient fish, it is necessary to use, as an indicator, a trait that is specifically expressed in the germ cell and can be used to distinguish the recipient fish from the donor fish. Vasa gene, which is a germ cell-specific gene, is specific to a primordial germ cell and a spermatogonium/an oogonium, and it is not expressed in a somatic cell. In the present invention, the Vasa gene sequences of a tuna, a chub mackerel, a spotted mackerel, an eastern little tuna, and a drumfish are determined, and the expression of such gene is used as a marker for a germ cell. In addition, according to the present invention, it is possible to specifically detect only a tuna Vasa gene in Vasa gene sequences that are highly conserved in fishes, without sequencing. Thus, a tuna-derived germ cell can be reliably and simply identified in the gonad of the recipient fish. As a result, the growth or breeding of tuna can be carried out with good efficiency. Moreover, utilizing the aforementioned findings, even in a case in which not only a tuna but also another Perciformes fish is used as a donor, a germ cell derived from the donor fish can be efficiently detected from the gonad of a recipient fish of a different species.

The invention claimed is:

1. An isolated DNA encoding a protein comprising the amino acid sequence shown in SEQ ID NO: 2 of the sequence listing.

2. An isolated DNA comprising the nucleotide sequence shown in SEQ ID NO: 1 of the sequence listing.

3. A recombinant vector comprising the DNA according to claim 1 or 2.

4. A fish cell transformed with the recombinant vector according to claim 3.

* * * * *

SEQUENCE LISTING

<160> NUMBER OF SEQ ID NOS: 24

<210> SEQ ID NO 1
<211> LENGTH: 2394
<212> TYPE: DNA
<213> ORGANISM: Bluefin tuna

<400> SEQUENCE: 1

```
ctacacaaat cagcgaccgg actgataaca ccatagactt ctgcttgaga agcttttgat      60
aagtgaaaaa agatggatga gtgggaagaa gagggaaata ctagcactat tacactaacc     120
agccgcacct caagtgaagg cacacaagga gacttctgga acaccaatgg tggtgaattt     180
ggaagggtc gcggtggaag aggcagaggg agaggaggat ttaaaagctc atactcctca      240
ggtggagatg ggaatgatga ggacaaatgg aacaatgcag gaggagaaag aggtggtttc     300
agaggtagag gaggccaagg gcgcggcaga ggattttgca gaatggatca aagtgaattc     360
aatggagatg acaatggaat gcgtgaaaat gggtatagag gaggaagagg gggcagagga    420
agaggaggag gtttcagcca aggtggcgac cagggtggca gaggaggctt tggaggaggt    480
tatcgtggaa aagatgagga gatctttact cgaggggaag ataaagatcc agaaaagaag    540
gacgatagtg acagaccaaa gatcacatat gttcccccaa ccctccctga agatgaggac    600
tccattttt cccactatga aacagggatc aactttgaca agtatgatga catcatggtg     660
gatgttagtg gaaccaatcc accacaagct gtcatgactt tgatgaggc agcattgtgc     720
gagtccctga gaaaaacgt cagcaagtct ggttatgtga agccgacccc tgtgcagaag     780
cacggcatcc caatcatctc tgctggtaga gatctcatgg cctgtgccca gactggatct    840
ggtaaaacgg ctgcattcct gctccctatt ctgcagcagc tgatgcagat ggtgtggca     900
gcaagtcgct tcagcgagct gcaggagcct gaagcaatca ttgtggcccc aaccagggag    960
ctcatcaacc agatttacct ggaggccagg aagtttgcct ttgggacatg tgtgcgtcca   1020
gtggtggttt atggtggagt cagcactgga caccaaataa gagaaatcga aagggatgc    1080
aatgtagtgt gtggaacacc agggaggcta ttggatatga ttggaagagg aaaggttggg   1140
ttgagtaagc tgcggtactt ggtgctagat gaggccgacc ggatgttgga tatgggattt   1200
gagcctgaca tgccccgcct ggtgggctca cctggaatgc catccaaaga gaaccgtcag   1260
actctgatgt tcagtgccac ataccctgaa gacatccaga ggatggcggc tgacttcctc   1320
aagacagact atttgttcct ggctgtgggt gtggtgggtg gagcctgcag tgatgtggag   1380
cagacattta tccaagtcac aaagttctcc aagagagagc agctccttga cctcctgaag   1440
accactggaa cggagcgcac catggtgttt gtagagacca aacgacaagc tgatttatt    1500
gccacgttct tgtgccaaga gaaagttcca actaccagca ttcacggtga ccgagagcag   1560
cgggagcgag agcaggctct ggcagacttc cgctctggta aatgtccagt cctagtagca   1620
acctctgtag ctgcccgcgg tctggatatt ccagatgtac agcatgtggt taactttgac   1680
ctccccaaca acattgatga atatgtccac cgtattggga ggactggccg ctgcggtaac   1740
acagggaggg cagtgtcttt ctatgaccct gatgctgatg ccaactggc tcgctccttg   1800
```

```
gtcacagtcc tgtccaaggc ccagcaggaa gtgccttcat ggttagaaga gtctgcgttc   1860
agcggacctg ctaccactgg ctttaaccca cctaggaaga actttgcctc cacagactcc   1920
aggaagagag gatctttcca agacaacagt gtgaagagcc agccggctgt tcagactgca   1980
gcggatgatg atgaggaatg ggaatagagg agcagcacac ccacacagca ttgacctgag   2040
ttgcttttta ttttcaggtg ttcagtttgt tgtagtttta tcacgtttct gtttgaatat   2100
agaaaaagtt tgtctcatgc cggacaaagt taaaaatgtc aagtgaggtg ttaaatggga   2160
aaaccagttt ttttttgtgt gatctgtcat ttccattctt cactgactgg cattttgtga   2220
agtttgtttt attttttatt gttttaatca tcacttgcat ttaaaatgtt taaaaaagga   2280
aactgtgtct gacgaccaaa agtaaaaact tataaatgtc aattatattt tgttttctac   2340
tcagaaaaag atcaataaat atttgttcaa agcaaaaaaa aaaaaaaaaa aaaa          2394

<210> SEQ ID NO 2
<211> LENGTH: 644
<212> TYPE: PRT
<213> ORGANISM: Bluefin tuna

<400> SEQUENCE: 2

Met Asp Glu Trp Glu Glu Gly Asn Thr Ser Thr Ile Thr Leu Thr
1               5                   10                  15

Ser Arg Thr Ser Ser Gly Thr Gln Gly Asp Phe Trp Asn Thr Asn
                20                  25                  30

Gly Gly Glu Phe Gly Arg Gly Arg Gly Arg Gly Arg Gly Arg Gly
            35                  40                  45

Gly Phe Lys Ser Ser Tyr Ser Ser Gly Gly Asp Gly Asn Asp Glu Asp
        50                  55                  60

Lys Trp Asn Asn Ala Gly Gly Glu Arg Gly Gly Phe Arg Gly Arg Gly
65                  70                  75                  80

Gly Gln Gly Arg Gly Arg Gly Phe Cys Arg Met Asp Gln Ser Glu Phe
                85                  90                  95

Asn Gly Asp Asp Asn Gly Met Arg Glu Asn Gly Tyr Arg Gly Gly Arg
            100                 105                 110

Gly Gly Arg Gly Arg Gly Gly Phe Ser Gln Gly Gly Asp Gln Gly
        115                 120                 125

Gly Arg Gly Gly Phe Gly Gly Tyr Arg Gly Lys Asp Glu Glu Ile
        130                 135                 140

Phe Thr Arg Gly Glu Asp Lys Asp Pro Glu Lys Lys Asp Asp Ser Asp
145                 150                 155                 160

Arg Pro Lys Ile Thr Tyr Val Pro Pro Thr Leu Pro Glu Asp Glu Asp
                165                 170                 175

Ser Ile Phe Ser His Tyr Glu Thr Gly Ile Asn Phe Asp Lys Tyr Asp
            180                 185                 190

Asp Ile Met Val Asp Val Ser Gly Thr Asn Pro Pro Gln Ala Val Met
        195                 200                 205

Thr Phe Asp Glu Ala Ala Leu Cys Glu Ser Leu Arg Lys Asn Val Ser
    210                 215                 220

Lys Ser Gly Tyr Val Lys Pro Thr Pro Val Gln Lys His Gly Ile Pro
225                 230                 235                 240

Ile Ile Ser Ala Gly Arg Asp Leu Met Ala Cys Ala Gln Thr Gly Ser
                245                 250                 255

Gly Lys Thr Ala Ala Phe Leu Leu Pro Ile Leu Gln Gln Leu Met Ala
            260                 265                 270

Asp Gly Val Ala Ala Ser Arg Phe Ser Glu Leu Gln Glu Pro Glu Ala
```

```
                275                 280                 285
Ile Ile Val Ala Pro Thr Arg Glu Leu Ile Asn Gln Ile Tyr Leu Glu
290                 295                 300

Ala Arg Lys Phe Ala Phe Gly Thr Cys Val Arg Pro Val Val Val Tyr
305                 310                 315                 320

Gly Gly Val Ser Thr Gly His Gln Ile Arg Glu Ile Glu Arg Gly Cys
                325                 330                 335

Asn Val Val Cys Gly Thr Pro Gly Arg Leu Leu Asp Met Ile Gly Arg
                340                 345                 350

Gly Lys Val Gly Leu Ser Lys Leu Arg Tyr Leu Val Leu Asp Glu Ala
355                 360                 365

Asp Arg Met Leu Asp Met Gly Phe Glu Pro Asp Met Arg Arg Leu Val
370                 375                 380

Gly Ser Pro Gly Met Pro Ser Lys Glu Asn Arg Gln Thr Leu Met Phe
385                 390                 395                 400

Ser Ala Thr Tyr Pro Glu Asp Ile Gln Arg Met Ala Ala Asp Phe Leu
                405                 410                 415

Lys Thr Asp Tyr Leu Phe Leu Ala Val Gly Val Val Gly Ala Cys
                420                 425                 430

Ser Asp Val Glu Gln Thr Phe Ile Gln Val Thr Lys Phe Ser Lys Arg
435                 440                 445

Glu Gln Leu Leu Asp Leu Leu Lys Thr Thr Gly Thr Glu Arg Thr Met
450                 455                 460

Val Phe Val Glu Thr Lys Arg Gln Ala Asp Phe Ile Ala Thr Phe Leu
465                 470                 475                 480

Cys Gln Glu Lys Val Pro Thr Thr Ser Ile His Gly Asp Arg Glu Gln
                485                 490                 495

Arg Glu Arg Glu Gln Ala Leu Ala Asp Phe Arg Ser Gly Lys Cys Pro
                500                 505                 510

Val Leu Val Ala Thr Ser Val Ala Ala Arg Gly Leu Asp Ile Pro Asp
                515                 520                 525

Val Gln His Val Val Asn Phe Asp Leu Pro Asn Asn Ile Asp Glu Tyr
530                 535                 540

Val His Arg Ile Gly Arg Thr Gly Arg Cys Gly Asn Thr Gly Arg Ala
545                 550                 555                 560

Val Ser Phe Tyr Asp Pro Asp Ala Asp Gly Gln Leu Ala Arg Ser Leu
                565                 570                 575

Val Thr Val Leu Ser Lys Ala Gln Gln Glu Val Pro Ser Trp Leu Glu
                580                 585                 590

Glu Ser Ala Phe Ser Gly Pro Ala Thr Thr Gly Phe Asn Pro Pro Arg
                595                 600                 605

Lys Asn Phe Ala Ser Thr Asp Ser Arg Lys Arg Gly Ser Phe Gln Asp
                610                 615                 620

Asn Ser Val Lys Ser Gln Pro Ala Val Gln Thr Ala Ala Asp Asp
625                 630                 635                 640

Glu Glu Trp Glu

<210> SEQ ID NO 3
<211> LENGTH: 2413
<212> TYPE: DNA
<213> ORGANISM: Scomber japonicus

<400> SEQUENCE: 3
acacggcacc agacggctta gtgaccagac ggagaacaac gacttctgct gagaaccttt      60
```

```
tgataagtta acaaaatgga tgagtgggaa gaagagggaa ccgttagtac tattccatta    120
accagctaca cctcgaatga aggcacacaa ggagactcct ggaacactga tgctggtgaa    180
tgtgcaaggg gtcgcggagg aagaggaaga gggagaggag gatttaaaag ctcatactct    240
tcaggtggag atgggaatga tggggacaaa tggaacaatg caggaggaga aagaggtggt    300
ttcagaggta gaggcggcca agggcgtggc agaggatttg gaagaacaga tcacagtgaa    360
gtcaatggac acgacagtgg agtgtgtgaa acgggtttc gaggagggag aggggcaga    420 ggaagaggag gaagtttcag tcaaggtcgg gacccgggtg gcagaggagg ctttggagga    480
ggttatcggg gaaagatgag agagatcttt tctcaagggg aagataaaga tcaagaaaag    540
aaggatgaca gtgagagacc aaaggtcacg tatgtgcccc ccacactccc cgaagatgaa    600
gactcaattt tttcccatta tgaaacgggg atcaactttg acaagtatga tgatatcatg    660
gtggatgtta gtggaaccaa tccaccacaa gctatcatga cttttgatga ggcggaattg    720
tgcgagtccc tgagaaaaaa tgtcagcaag tctggttatg tgaagccgac cccagtgcag    780
aaacatggca ttccaattat ctctgctggc agagatctca tggcctgtgc ccagactgga    840
tctggtaaaa cggctgcatt cctgctccct attctgcagc agctgatggc agatggtgtt    900
gcagccagtc gcttcagtga gctgcaggag cctgaagcaa ttattgtggc cccaacaagg    960
gagctcatta accagattta cctggaggct aggaagtttg cctttgggac atgtgtgcgt    1020
ccagtggtgg tttatggtgg agtcagcact ggacaccaaa taagagacat tgaaagggga    1080
tgcaatgtag tgtgtggaac accaggcagg ctattggata tgattggtag aggaaaggtt    1140
ggggtgagta agctgcggta cctagtccta gatgaggctg accggatgtt ggatatggga    1200
tttgagcctg atatgcgccg cttggtgggc tcacctggaa tgccatccaa agaggaccgt    1260
cagactctta tgttcagtgc tacgtaccct gaggacatac agaggatggc tgctgacttc    1320
ctgaagaccg actatttgtt cctggctgtg ggtgtggtgg gtggagcctg cagtgatgtg    1380
gagcagacat ttatccaagt caccaagttc tccaagagag agcaacttct tgacctcctg    1440
aagaccactg gaatggagcg caccatggtg tttgtggaga ccaagagaca agctgatttt    1500
atcgccacgt tcttgtgcca ggagaaagtt ccaaccacta gcattcatgg tgatcgagag    1560
cagcgggagc gagagcaagc tctggcagac ttccgctctg gtaaatgtcc agtcatggtg    1620
gcaacctctg tagctgcccg tggtctggat attccagatg tacagcatgt ggtgaacttt    1680 gacctccca caacattga tgaatatgtt caccgtattg ggagaactgg ccgctgcggt    1740
aatactggga gggcagtgtc tttctatgac cctgatggtg atagccaact ggcttgctcc    1800
ttggtcacag tcctgtccaa ggcccagcag gaagtgcctt catggttaga agagtctgcg    1860
ttcagcggat ctacttcctc tagcttcaaa ccacccagga gaactttgc ctccacagac    1920 tccaggaagg gaggatcttt ccaagacagt gtgcagagcc aggaggctgt tcagcctgct    1980
gccaatgatg atgaagaatg gaatagaag aacagcacat aagcattgac cacacagcat    2040
tgacctgagt tactttttat tttcaggtgt tcagcttctt gtagttttat catagtgttt    2100
ttgttggaat acaaaaaaag tttcttgtca gacaaagttt aaaatgctaa gtgagatggt    2160
aaatggtgaa accagttttt tgtttttttc tatgatctgt catctccatt cactgactgg    2220
cactttgtga acattttctt tttctttttt tattgtttta atcatcactt acatttaaag    2280
tgtttaaaaa agtaaacaat gtgtctgatg gcaaaaagca aaactttga aatgtcatat    2340 attttgtttt ctacgaggat aaagataaat aaatatttgt tctaagcaaa aaaaaaaaa    2400 aaaaaaaaaa aaa                                                       2413
```

<210> SEQ ID NO 4
<211> LENGTH: 643
<212> TYPE: PRT
<213> ORGANISM: Scomber japonicus

<400> SEQUENCE: 4

```
Met Asp Glu Trp Glu Glu Gly Thr Val Ser Thr Ile Pro Leu Thr
 1               5                  10                  15

Ser Tyr Thr Ser Asn Glu Gly Thr Gln Gly Asp Ser Trp Asn Thr Asp
            20                  25                  30

Ala Gly Glu Cys Ala Arg Gly Arg Gly Gly Arg Gly Arg Gly
            35                  40                  45

Gly Phe Lys Ser Ser Tyr Ser Ser Gly Gly Asp Gly Asn Asp Gly Asp
    50                  55                  60

Lys Trp Asn Asn Ala Gly Gly Glu Arg Gly Gly Phe Arg Gly Arg Gly
 65                  70                  75                  80

Gly Gln Gly Arg Gly Arg Gly Phe Gly Arg Thr Asp His Ser Glu Val
                85                  90                  95

Asn Gly Asp Asp Ser Gly Val Cys Glu Asn Gly Phe Arg Gly Gly Arg
            100                 105                 110

Gly Gly Arg Gly Arg Gly Gly Ser Phe Ser Gln Gly Arg Asp Pro Gly
            115                 120                 125

Gly Arg Gly Gly Phe Gly Gly Tyr Arg Gly Lys Asp Glu Glu Ile
            130                 135                 140

Phe Ser Gln Gly Glu Asp Lys Asp Gln Glu Lys Lys Asp Asp Ser Glu
145                 150                 155                 160

Arg Pro Lys Val Thr Tyr Val Pro Pro Thr Leu Pro Glu Asp Glu Asp
                165                 170                 175

Ser Ile Phe Ser His Tyr Glu Thr Gly Ile Asn Phe Asp Lys Tyr Asp
            180                 185                 190

Asp Ile Met Val Asp Val Ser Gly Thr Asn Pro Pro Gln Ala Ile Met
            195                 200                 205

Thr Phe Asp Glu Ala Glu Leu Cys Glu Ser Leu Arg Lys Asn Val Ser
210                 215                 220

Lys Ser Gly Tyr Val Lys Pro Thr Pro Val Gln Lys His Gly Ile Pro
225                 230                 235                 240

Ile Ile Ser Ala Gly Arg Asp Leu Met Ala Cys Ala Gln Thr Gly Ser
                245                 250                 255

Gly Lys Thr Ala Ala Phe Leu Leu Pro Ile Leu Gln Gln Leu Met Ala
            260                 265                 270

Asp Gly Val Ala Ala Ser Arg Phe Ser Glu Leu Gln Glu Pro Glu Ala
            275                 280                 285

Ile Ile Val Ala Pro Thr Arg Glu Leu Ile Asn Gln Ile Tyr Leu Glu
            290                 295                 300

Ala Arg Lys Phe Ala Phe Gly Thr Cys Val Arg Pro Val Val Tyr
305                 310                 315                 320

Gly Gly Val Ser Thr Gly His Gln Ile Arg Asp Ile Glu Arg Gly Cys
                325                 330                 335

Asn Val Val Cys Gly Thr Pro Gly Arg Leu Leu Asp Met Ile Gly Arg
            340                 345                 350

Gly Lys Val Gly Val Ser Lys Leu Arg Tyr Leu Val Leu Asp Glu Ala
            355                 360                 365

Asp Arg Met Leu Asp Met Gly Phe Glu Pro Asp Met Arg Arg Leu Val
            370                 375                 380
```

-continued

```
Gly Ser Pro Gly Met Pro Ser Lys Glu Asp Arg Gln Thr Leu Met Phe
385                 390                 395                 400
Ser Ala Thr Tyr Pro Glu Asp Ile Gln Arg Met Ala Ala Asp Phe Leu
            405                 410                 415
Lys Thr Asp Tyr Leu Phe Leu Ala Val Gly Val Gly Gly Ala Cys
        420                 425                 430
Ser Asp Val Glu Gln Thr Phe Ile Gln Val Thr Lys Phe Ser Lys Arg
        435                 440                 445
Glu Gln Leu Leu Asp Leu Leu Lys Thr Thr Gly Met Glu Arg Thr Met
    450                 455                 460
Val Phe Val Glu Thr Lys Arg Gln Ala Asp Phe Ile Ala Thr Phe Leu
465                 470                 475                 480
Cys Gln Glu Lys Val Pro Thr Thr Ser Ile His Gly Asp Arg Glu Gln
                485                 490                 495
Arg Glu Arg Glu Gln Ala Leu Ala Asp Phe Arg Ser Gly Lys Cys Pro
            500                 505                 510
Val Met Val Ala Thr Ser Val Ala Ala Arg Gly Leu Asp Ile Pro Asp
        515                 520                 525
Val Gln His Val Val Asn Phe Asp Leu Pro Asn Asn Ile Asp Glu Tyr
    530                 535                 540
Val His Arg Ile Gly Arg Thr Gly Arg Cys Gly Asn Thr Gly Arg Ala
545                 550                 555                 560
Val Ser Phe Tyr Asp Pro Asp Gly Asp Ser Gln Leu Ala Cys Ser Leu
                565                 570                 575
Val Thr Val Leu Ser Lys Ala Gln Gln Glu Val Pro Ser Trp Leu Glu
            580                 585                 590
Glu Ser Ala Phe Ser Gly Ser Thr Ser Ser Phe Lys Pro Pro Arg
        595                 600                 605
Lys Asn Phe Ala Ser Thr Asp Ser Arg Lys Gly Gly Ser Phe Gln Asp
    610                 615                 620
Ser Val Gln Ser Gln Glu Ala Val Gln Pro Ala Ala Asn Asp Asp Glu
625                 630                 635                 640
Glu Trp Glu

<210> SEQ ID NO 5
<211> LENGTH: 2435
<212> TYPE: DNA
<213> ORGANISM: Scomber australasicus

<400> SEQUENCE: 5
ggaagtggca accctacagg tcggagtgca aagtgtgcac acggcaccag acggcttagt        60
gaccagacgg agaacaacga cttctgcgga ggagcttttg ataagttaac aaaaatggat      120
gagtgggaag aagagggaac cgttagtact attccattaa ccagctacac cccgaatgaa      180
ggcacacaag gagactcctg gaacactgat gctggtgaat gtgcaagggg tcgcggagga      240
agaggcagag ggagaggagg atttaaaagc tcatactctt caggtggaga tgggaatgat      300
ggggacaaat ggacaatgc aggaggagaa agagtggtt tcagaggtag aggcggccaa        360
gggcgtggca gaggatttgg aagaacagat cacagtgaag tcaatggaga cgacagtgga      420
gtgtgtgaaa cgggtttcg aggaggcaga gggggtagag aagaggagg aagtttcagt        480 caaggtcggg actcgggtgg cagaggaggc tttggaggag gttatcgtgg aaaagatgaa      540
gagatctttt ctcaagggga agataaagat caagacaaga aggatgacag tgagagacca      600
aaggtcacgt atgtgccccc cacactccct gaagatgaag actcaatttt ttcccattat      660
```

```
gaaacgggga tcaactttga caagtatgat gatatcatgg tggatgttag tggaaccaat    720
ccaccacaag ctatcatgac ttttgatgag gcgcaattgt gcgagtccct gagaaaaaat    780
gtcagcaagt ctggttatgt gaagccgacc ccagtgcaga acatggcat tccaatcatc    840 tctgctggca gagatctcat ggcctgtgcc cagactggat ctggtaaaac ggctgcattc    900
ctgctcccta ttctgcagca gctgatggca gatggtgttg cagccagtcg cttcagtgag    960
ctgcaggagc ctgaagcaat tattgtggcc caacaaggg agctcatcaa ccagatttac   1020
ctggaggcta ggaagtttgc ctttgggaca tgtgtgcgtc ctgtggtggt ttatggtgga   1080
gtcagcactg acaccaaat aagagacatt gaaggggat gcaatatagt gtgtggaaca    1140
ccaggcaggc tattggatat gattggtaga ggaaaggttg gggtgagtaa gctgcggtac   1200
ctagtcctag atgaggctga ccggatgttg gatatgggat tgagcctga tatgcgccgc   1260 ttggtgggct cacctggaat gccatccaaa gagaaccgtc agactcttat gttcagtgct   1320
acgtaccctg aggacataca gaggatggct gctgacttcc tgaagaccga ctatttgttc   1380
ctggctgtgg gtgtggtggg tggagcctgc agtgatgtgg agcagacgtt tatccaagtc   1440
accaagttct ccaagagaga gcaacttctt gacctcctga agaccactgg aatggagcgc   1500
accatggtgt ttgtggagac caagagacaa gctgatttta tcgccacgtt cttgtgccag   1560
gagaaagttc caaccactag cattcatggt gatcgagagc agcgggagcg agagcaagct   1620
ctggcagact tccgctctgg taaatgtcca gtcatggtgg caacctctgt agctgcccgt   1680
ggtctggata ttccagatgt acagcatgtg gtgaactttg acctccccaa caacattgat   1740
gaatatgttc accgtattgg gagaactggc cgctgcggta atactgggag ggcagtgtct   1800
ttctatgacc ctgatggtga tagccaactg gctagctcct tggtcacagt cctgtccaag   1860
gcccagcagg aagtgccttc atggttagaa gagtctgcgt tcagcggatc tacttcctct   1920
agcttcaaac cacccaggaa gaactttgcc tccacagact ccaggaaggg aggatctttc   1980
caagacaaca gtatgcagag ccaggaggct gttcagcctg ctgccaatga tgatgatgaa   2040
gaatgggaat agaagaacag cacaaccaca cagcaatgac ctgagttact tttattttc    2100 aggtgttcag cttcttgtag ttttatcaca gtgttttgt tggaatatta aaaagttc     2160 ttgtcagaca aagtttaaaa tgctaagtga gatggtaaat ggcgaaacca gttttttgt    2220 ttttgtatga tctgtcttct ccattcactg actggcactt tgtgaacatt tcttttct    2280 tttttattgt tttaatcatc acttacattt aaagtgttta aaaagtaaa caatgtgtct    2340 gatggcaaaa agcaaaactt tgaaatgtc atatattttg ttttctacga ggataaagat   2400
aaataaatat ttgttctaag caaaaaaaaa aaaaa                              2435
```

<210> SEQ ID NO 6
<211> LENGTH: 645
<212> TYPE: PRT
<213> ORGANISM: Scomber australasicus

<400> SEQUENCE: 6

```
Met Asp Glu Trp Glu Glu Glu Gly Thr Val Ser Thr Ile Pro Leu Thr
1               5                   10                  15

Ser Tyr Thr Pro Asn Glu Gly Thr Gln Gly Asp Ser Trp Asn Thr Asp
                20                  25                  30

Ala Gly Glu Cys Ala Arg Gly Arg Gly Gly Arg Gly Arg Gly Arg Gly
            35                  40                  45

Gly Phe Lys Ser Ser Tyr Ser Ser Gly Gly Asp Gly Asn Asp Gly Asp
        50                  55                  60
```

```
Lys Trp Asn Asn Ala Gly Gly Glu Arg Gly Gly Phe Arg Gly Arg Gly
 65                  70                  75                  80

Gly Gln Gly Arg Gly Arg Gly Phe Gly Arg Thr Asp His Ser Glu Val
                 85                  90                  95

Asn Gly Asp Asp Ser Gly Val Cys Glu Asn Gly Phe Arg Gly Gly Arg
             100                 105                 110

Gly Gly Arg Gly Arg Gly Gly Ser Phe Ser Gln Gly Arg Asp Ser Gly
             115                 120                 125

Gly Arg Gly Gly Phe Gly Gly Tyr Arg Gly Lys Asp Glu Glu Ile
         130                 135                 140

Phe Ser Gln Gly Glu Asp Lys Asp Gln Asp Lys Lys Asp Ser Glu
145                 150                 155                 160

Arg Pro Lys Val Thr Tyr Val Pro Pro Thr Leu Pro Glu Asp Glu Asp
                 165                 170                 175

Ser Ile Phe Ser His Tyr Glu Thr Gly Ile Asn Phe Asp Lys Tyr Asp
             180                 185                 190

Asp Ile Met Val Asp Val Ser Gly Thr Asn Pro Pro Gln Ala Ile Met
         195                 200                 205

Thr Phe Asp Glu Ala Gln Leu Cys Glu Ser Leu Arg Lys Asn Val Ser
210                 215                 220

Lys Ser Gly Tyr Val Lys Pro Thr Pro Val Gln Lys His Gly Ile Pro
225                 230                 235                 240

Ile Ile Ser Ala Gly Arg Asp Leu Met Ala Cys Ala Gln Thr Gly Ser
                 245                 250                 255

Gly Lys Thr Ala Ala Phe Leu Leu Pro Ile Leu Gln Gln Leu Met Ala
             260                 265                 270

Asp Gly Val Ala Ala Ser Arg Phe Ser Glu Leu Gln Glu Pro Glu Ala
         275                 280                 285

Ile Ile Val Ala Pro Thr Arg Glu Leu Ile Asn Gln Ile Tyr Leu Glu
         290                 295                 300

Ala Arg Lys Phe Ala Phe Gly Thr Cys Val Arg Pro Val Val Val Tyr
305                 310                 315                 320

Gly Gly Val Ser Thr Gly His Gln Ile Arg Asp Ile Glu Arg Gly Cys
                 325                 330                 335

Asn Ile Val Cys Gly Thr Pro Gly Arg Leu Leu Asp Met Ile Gly Arg
             340                 345                 350

Gly Lys Val Gly Val Ser Lys Leu Arg Tyr Leu Val Leu Asp Glu Ala
         355                 360                 365

Asp Arg Met Leu Asp Met Gly Phe Glu Pro Asp Met Arg Arg Leu Val
370                 375                 380

Gly Ser Pro Gly Met Pro Ser Lys Glu Asn Arg Gln Thr Leu Met Phe
385                 390                 395                 400

Ser Ala Thr Tyr Pro Glu Asp Ile Gln Arg Met Ala Ala Asp Phe Leu
                 405                 410                 415

Lys Thr Asp Tyr Leu Phe Leu Ala Val Gly Val Val Gly Gly Ala Cys
             420                 425                 430

Ser Asp Val Glu Gln Thr Phe Ile Gln Val Thr Lys Phe Ser Lys Arg
         435                 440                 445

Glu Gln Leu Leu Asp Leu Leu Lys Thr Thr Gly Met Glu Arg Thr Met
450                 455                 460

Val Phe Val Glu Thr Lys Arg Gln Ala Asp Phe Ile Ala Thr Phe Leu
465                 470                 475                 480

Cys Gln Glu Lys Val Pro Thr Thr Ser Ile His Gly Asp Arg Glu Gln
                 485                 490                 495
```

```
Arg Glu Arg Glu Gln Ala Leu Ala Asp Phe Arg Ser Gly Lys Cys Pro
            500                 505                 510

Val Met Val Ala Thr Ser Val Ala Ala Arg Gly Leu Asp Ile Pro Asp
        515                 520                 525

Val Gln His Val Val Asn Phe Asp Leu Pro Asn Asn Ile Asp Glu Tyr
    530                 535                 540

Val His Arg Ile Gly Arg Thr Gly Arg Cys Gly Asn Thr Gly Arg Ala
545                 550                 555                 560

Val Ser Phe Tyr Asp Pro Asp Gly Asp Ser Gln Leu Ala Ser Ser Leu
                565                 570                 575

Val Thr Val Leu Ser Lys Ala Gln Gln Glu Val Pro Ser Trp Leu Glu
            580                 585                 590

Glu Ser Ala Phe Ser Gly Ser Thr Ser Ser Ser Phe Lys Pro Pro Arg
        595                 600                 605

Lys Asn Phe Ala Ser Thr Asp Ser Arg Lys Gly Gly Ser Phe Gln Asp
    610                 615                 620

Asn Ser Met Gln Ser Gln Glu Ala Val Gln Pro Ala Ala Asn Asp Asp
625                 630                 635                 640

Asp Glu Glu Trp Glu
                645

<210> SEQ ID NO 7
<211> LENGTH: 2361
<212> TYPE: DNA
<213> ORGANISM: Euthynnus affinis

<400> SEQUENCE: 7
accagacggc ttagtgacca gacggagaac gacgacttct gcggaggagc ttttgataag      60
ttaacaaaaa tggatgagtg ggaagaagag ggaaccgtta gtactattcc attaaccagc     120
tacacctcga atgaaggcac acaaggagac tcctggaaca ctgatgctgg tgaatgtgca     180
aggggtcgcg gaggaagagg cagagggaga ggaggattta aaagctcata ctcttcaggt     240
ggagatggga atgatgggga caaatggaac aatgcaggag gagaaagagg tggtttcaga     300
ggtagaggcg gccaagggcg tggcagagga tttggaagaa cagatcacag tgaagtcaat     360
ggagacgaca gtggagtatg tgaaaacggg tttcgaggag ggagagggg tagaggaaga     420 ggaggaagtt tcagtcaagg tcgggactcg ggtggcagag gaggctttgg aggaggttat     480
cgtggaaaag atgaagagat ctttctcaa ggggaagata agatcaaga caagaaggat     540 gacagtgaga gaccaaaggt cacgtatgtg ccccccacac tccctgaaga tgaagactca     600
gttttttccc attatgaaac ggggatcaac tttgacaagt atgatgatat catggtggat     660
gttagtggaa ccaatccacc acaagctatc atgacttttg atgaggcgca attgtgcgag     720
tccctgagaa aaaatgtcag caagtctggt tatgtgaagc cgaccccagt gcagaaacat     780
ggcattccaa tcatctctgc tggcagagat ctcatggcct gtgcccagac tggatctggt     840
aaaacggctg cattcctgct ccctattctg cagcagctga tggcagatgg tgtggcagcc     900
agtcgcttca gcgagctgca ggagcctgaa gccatcattg tggccccaac cagggagctc     960
atcaaccaga tttacctgga agccaggaag tttgcctttg gacatgtgt gcgtccagtg    1020 gtggtttatg gtggagtcag cactggacac caaataagg aaatctcaag gggatgcaat    1080
gtagtgtgtg gaacacctgg gaggctattg gatatgattg aagaggaaa ggttgggttg    1140 actaagctgc ggtacctggt gctagatgag ccgacagga tgttggatat gggatttgag    1200
cctgacatgc gccggctggt gagctcacct ggaatgccat ccaaagagaa ccgtcagaca    1260
```

```
ctgatgttca gtgccacgta ccctgaagac atccagaggt tggcagctga cttcctcaag    1320
accgactatt tgttcctggc tgtgggtgtg gtgggtggag cctgcagtga tgtggagcag    1380
acatttatcc aagtaacaaa gttctccaag agagagcagc tccttgacct cctgaagacc    1440
actggaatgg agcgcaccat ggtgtttgtg agaccaaac gacaagctga ttttattgcc     1500
actttcttgt gccaggagaa agttccaact accagcattc atggtgacag agagcagcgg    1560
gagagagagc aggctctggc agacttccgc tccggtaaat gtcccgtcct agtggcaaca    1620
tctgtagctg cccgcggtct ggatattcca gatgtgcagc atgtggtgaa cttttgacctc   1680 cccaacaaca ttgatgaata tgtccaccgt attgggagaa ccggccgctg cggtaacact    1740
gggagggcag tgtcttttta tgaccctgat gctgatggcc aactggctcg ctccttggtc    1800
acggtcctgt ccaaggccca gcaggaagtg ccttcatggt tagaagagtc tgcattcagt    1860
ggacctgctg tcaccagctt caacccatcc aggaagacct tgcctccac agactccagg     1920 aagggaggat ctctccaaga caacagtgtg aagagccagc cggctgttca cactgcagct    1980
gatgatgagg aggaatggga atagaagagc agcgcaccca cacagcattg acctgaatta    2040 cttttattt tcaggcgttc agtttattgt agttttatca cgttttgtt tgaatataca      2100 agaaaagttt aaaatgtcaa gtgagatgtt aaatggggag accagttttt ttgtgtgatc    2160
tgtcatttcc attcactgac tggcattttg tgaagtttgt tttatttttt attgttttaa    2220
tcatcacttg catttaaaat gtttaaaaaa ggaaacaatg tgtcgaccaa aaagtaaaa     2280 cttataaatg tcaactatat tttgttttct actttgataa caatcaataa atatttgttc    2340
aaagcaaaaa aaaaaaaaaa a                                              2361
```

<210> SEQ ID NO 8
<211> LENGTH: 644
<212> TYPE: PRT
<213> ORGANISM: Euthynnus affinis

<400> SEQUENCE: 8

```
Met Asp Glu Trp Glu Glu Gly Thr Val Ser Thr Ile Pro Leu Thr
1               5                   10                  15

Ser Tyr Thr Ser Asn Glu Gly Thr Gln Gly Asp Ser Trp Asn Thr Asp
                20                  25                  30

Ala Gly Glu Cys Ala Arg Gly Arg Gly Gly Arg Gly Gly Arg Gly
            35                  40                  45

Gly Phe Lys Ser Ser Tyr Ser Ser Gly Gly Asp Gly Asn Asp Gly Asp
        50                  55                  60

Lys Trp Asn Asn Ala Gly Gly Glu Arg Gly Gly Phe Arg Gly Arg Gly
65                  70                  75                  80

Gly Gln Gly Arg Gly Arg Gly Phe Gly Arg Thr Asp His Ser Glu Val
                85                  90                  95

Asn Gly Asp Asp Ser Gly Val Cys Glu Asn Gly Phe Arg Gly Gly Arg
                100                 105                 110

Gly Gly Arg Gly Arg Gly Ser Phe Ser Gln Gly Arg Asp Ser Gly
            115                 120                 125

Gly Arg Gly Gly Phe Gly Gly Tyr Arg Gly Lys Asp Glu Glu Ile
        130                 135                 140

Phe Ser Gln Gly Glu Asp Lys Asp Gln Asp Lys Lys Asp Ser Glu
145                 150                 155                 160

Arg Pro Lys Val Thr Tyr Val Pro Pro Thr Leu Pro Glu Asp Glu Asp
                165                 170                 175
```

```
Ser Val Phe Ser His Tyr Glu Thr Gly Ile Asn Phe Asp Lys Tyr Asp
            180                 185                 190

Asp Ile Met Val Asp Val Ser Gly Thr Asn Pro Pro Gln Ala Ile Met
            195                 200                 205

Thr Phe Asp Glu Ala Gln Leu Cys Glu Ser Leu Arg Lys Asn Val Ser
210                 215                 220

Lys Ser Gly Tyr Val Lys Pro Thr Pro Val Gln Lys His Gly Ile Pro
225                 230                 235                 240

Ile Ile Ser Ala Gly Arg Asp Leu Met Ala Cys Ala Gln Thr Gly Ser
                245                 250                 255

Gly Lys Thr Ala Ala Phe Leu Leu Pro Ile Leu Gln Gln Leu Met Ala
                260                 265                 270

Asp Gly Val Ala Ala Ser Arg Phe Ser Glu Leu Gln Glu Pro Glu Ala
                275                 280                 285

Ile Ile Val Ala Pro Thr Arg Glu Leu Ile Asn Gln Ile Tyr Leu Glu
            290                 295                 300

Ala Arg Lys Phe Ala Phe Gly Thr Cys Val Arg Pro Val Val Val Tyr
305                 310                 315                 320

Gly Gly Val Ser Thr Gly His Gln Ile Arg Glu Ile Ser Arg Gly Cys
                325                 330                 335

Asn Val Val Cys Gly Thr Pro Gly Arg Leu Leu Asp Met Ile Gly Arg
                340                 345                 350

Gly Lys Val Gly Leu Thr Lys Leu Arg Tyr Leu Val Leu Asp Glu Ala
            355                 360                 365

Asp Arg Met Leu Asp Met Gly Phe Glu Pro Asp Met Arg Arg Leu Val
            370                 375                 380

Ser Ser Pro Gly Met Pro Ser Lys Glu Asn Arg Gln Thr Leu Met Phe
385                 390                 395                 400

Ser Ala Thr Tyr Pro Glu Asp Ile Gln Arg Leu Ala Ala Asp Phe Leu
                405                 410                 415

Lys Thr Asp Tyr Leu Phe Leu Ala Val Gly Val Val Gly Gly Ala Cys
            420                 425                 430

Ser Asp Val Glu Gln Thr Phe Ile Gln Val Thr Lys Phe Ser Lys Arg
            435                 440                 445

Glu Gln Leu Leu Asp Leu Leu Lys Thr Thr Gly Met Glu Arg Thr Met
450                 455                 460

Val Phe Val Glu Thr Lys Arg Gln Ala Asp Phe Ile Ala Thr Phe Leu
465                 470                 475                 480

Cys Gln Glu Lys Val Pro Thr Thr Ser Ile His Gly Asp Arg Glu Gln
                485                 490                 495

Arg Glu Arg Glu Gln Ala Leu Ala Asp Phe Arg Ser Gly Lys Cys Pro
                500                 505                 510

Val Leu Val Ala Thr Ser Val Ala Ala Arg Gly Leu Asp Ile Pro Asp
            515                 520                 525

Val Gln His Val Val Asn Phe Asp Leu Pro Asn Asn Ile Asp Glu Tyr
            530                 535                 540

Val His Arg Ile Gly Arg Thr Gly Arg Cys Gly Asn Thr Gly Arg Ala
545                 550                 555                 560

Val Ser Phe Tyr Asp Pro Asp Ala Asp Gly Gln Leu Ala Arg Ser Leu
                565                 570                 575

Val Thr Val Leu Ser Lys Ala Gln Gln Glu Val Pro Ser Trp Leu Glu
            580                 585                 590

Glu Ser Ala Phe Ser Gly Pro Ala Val Thr Ser Phe Asn Pro Ser Arg
            595                 600                 605
```

Lys Thr Phe Ala Ser Thr Asp Ser Arg Lys Gly Gly Ser Leu Gln Asp
    610                 615                 620

Asn Ser Val Lys Ser Gln Pro Ala Val His Thr Ala Ala Asp Asp Glu
625                 630                 635                 640

Glu Glu Trp Glu

<210> SEQ ID NO 9
<211> LENGTH: 2370
<212> TYPE: DNA
<213> ORGANISM: Nibea mitsukurii

<400> SEQUENCE: 9

```
ttcgccgagc tcttcttgag aagtacaagt tcacgagttg aacaaaatgg acgactggga      60
agaaggggaa gccgctagta ctgccgcgct gaccggccgc aacccaactg aaggcacaca     120
aggaggctcc tggaatactt tcagcggcga atttggaagg ggtcgcggtg ggagaggcag     180
aggggaggc tttaaagccg cgttctcttc aggcacggat gagaacgcga acggggacga     240
cggggacaac tggaacaaca cagaagggga acgaggtggt ttcagaggta gaggtggcag     300
aggccgtggc aggggattcg gcaggacgga tcgcagcgaa ttcagtggag aggacggcgt     360
gtgcgaaaac ggctttagag gagggagcag aggaggaaga ggaggcagag gaggaggagg     420
aggtttcaga tcaggtgatg accagggtgg cagaggaggc tttggaggag gggaagacaa     480
agaaaataag gatggaagcg atggtgaccg accccgggtc acgtacattc ccccgaccct     540
gcctgaagac gaagacacca ttttgcccca ctataagacg ggcatcaact ttgacaagta     600
tgacgacatc atggtggatg tgagcggaac caatgcgcca caggctatca tgacctttga     660
agaggcaaca ctgtgcgagt ccctgagaaa agccgtcgcc aagtctggct acgtgaagcc     720
gaccctgtg cagaagcacg ggatcccgat catctctgct ggcagagatc tcatggcctg     780
cgctcagacc ggatctggta aaacggctgc gttcctgctc cccattctgc agcagctgat     840
ggcggacggc gtggcagcca gctccttcag cgagctgcag gagcctgaag tcctcatcgt     900
ggccccaacc agggagctca tcaaccagat ttacatggag gcccggaagt ctcctatgg     960
gacatgcgtg cgtccagtag tggtttatgg cggagttagc accggatacc aaatacggga    1020
aatctcacgg gggtgcaatg tgctgtgtgg aacaccgggg agactgttgg acgtgattgg    1080
aagaggaaag attggcttga gcaagctgcg gtactttgtg ctggacgagg ctgaccgcat    1140
gttggacatg ggcttcgaac cggacatgcg ccgtttggtg ggctccccg gcatgccgac    1200
caaagagcac cgccagaccc tgatgttcag tgccacgtac cccgaggaca tccagaggat    1260
ggctgctgac ttcctgaaga ccgactattt gttcttggcc gtgggtgtgg tgggcggagc    1320
ctgcagtgac gtggagcaga catttgtcca agtcacaaag ttctccaaga gggagcaact    1380
cctcgacctc ctgaagacaa ctggaacgga gcgcaccatg gtgtttgtgg agaccaagag    1440
gcaagctgat tcatcgcga cgtacctgtg ccaggagaaa gttccaacaa ccagcattca    1500
tggcgaccgt gagcagcgcg agcgggagca ggctctggcg gacttccgct ccggcaagtg    1560
tccggtcctg gtggcgacct ccgtagctgc ccgcggcctg gatgttcccg acgtactgaa    1620
cgtagtgagc tttgacctcc ccaacaacat cgacgaatat gtccaccgca ttgggaggac    1680
cggccgctgc gggaacactg gcagagccgt gtctttctat gacccagatg ctgatgggca    1740
gctggctcgc tcgctcgtca caatcctgtc caaggcccag caggaagtgc cctcgtggtt    1800
agaagagtat gcgttcagcg tcccgggtga cgcgggcttc aactcctcca agaggaactt    1860
tgcctcctca gactccagga agggtcatca tggaggatct tttcaggaca acggtgcgac    1920
```

-continued

```
gagccagccg gccgctcagg ccgcggctga cgacgatgac tgggagtaga ggggatatga    1980
acagcagacc gccacacatc cgtgacctga gttgttttc ttggcaggtg tccagcttgt    2040
tgccgtttta ttatcacagt gttttgttt aaaaagggag aaaaacgtgt ttgcctcaag    2100
gccgtacgaa atttaaaaaa aaaaaacgtc ccgtgagacg ttaaacgtgg gaaccagtga    2160 caactttca gtcttcactg agcagcagat tgtgtaaagt tagttttta ttttatttt     2220 ttatcacttg catgtaacgt gatgaaggaa acaatggac cctgaccaga ggtcaaacat    2280
ggaaggctgt tatattccaa ctcttaattt gtttcctgtg agcatgaaaa ttaataaata    2340
cgtaatttgt tcaaaaaaaa aaaaaaaaaa                                    2370
```

<210> SEQ ID NO 10
<211> LENGTH: 640
<212> TYPE: PRT
<213> ORGANISM: Nibea mitsukurii

<400> SEQUENCE: 10

```
Met Asp Asp Trp Glu Glu Gly Glu Ala Ala Ser Thr Ala Ala Leu Thr
1               5                   10                  15

Gly Arg Asn Pro Thr Glu Gly Thr Gln Gly Gly Ser Trp Asn Thr Phe
            20                  25                  30

Ser Gly Glu Phe Gly Arg Gly Arg Gly Gly Arg Gly Gly Gly Gly Gly
        35                  40                  45

Phe Lys Ala Ala Phe Ser Ser Gly Thr Asp Glu Asn Ala Asn Gly Asp
    50                  55                  60

Asp Gly Asp Asn Trp Asn Asn Thr Glu Gly Glu Arg Gly Gly Phe Arg
65                  70                  75                  80

Gly Arg Gly Gly Arg Gly Arg Gly Arg Gly Phe Gly Arg Thr Asp Arg
                85                  90                  95

Ser Glu Phe Ser Gly Glu Asp Gly Val Cys Glu Asn Gly Phe Arg Gly
            100                 105                 110

Gly Ser Arg Gly Gly Arg Gly Gly Arg Gly Gly Gly Gly Phe Arg
        115                 120                 125

Ser Gly Asp Asp Gln Gly Gly Arg Gly Gly Phe Gly Gly Gly Glu Asp
    130                 135                 140

Lys Glu Asn Lys Asp Gly Ser Asp Gly Asp Arg Pro Arg Val Thr Tyr
145                 150                 155                 160

Ile Pro Pro Thr Leu Pro Glu Asp Glu Asp Thr Ile Phe Ala His Tyr
                165                 170                 175

Lys Thr Gly Ile Asn Phe Asp Lys Tyr Asp Asp Ile Met Val Asp Val
            180                 185                 190

Ser Gly Thr Asn Ala Pro Gln Ala Ile Met Thr Phe Glu Glu Ala Thr
        195                 200                 205

Leu Cys Glu Ser Leu Arg Lys Ala Val Ala Lys Ser Gly Tyr Val Lys
    210                 215                 220

Pro Thr Pro Val Gln Lys His Gly Ile Pro Ile Ile Ser Ala Gly Arg
225                 230                 235                 240

Asp Leu Met Ala Cys Ala Gln Thr Gly Ser Gly Lys Thr Ala Ala Phe
                245                 250                 255

Leu Leu Pro Ile Leu Gln Gln Leu Met Ala Asp Gly Val Ala Ala Ser
            260                 265                 270

Ser Phe Ser Glu Leu Gln Glu Pro Glu Val Leu Ile Val Ala Pro Thr
        275                 280                 285

Arg Glu Leu Ile Asn Gln Ile Tyr Met Glu Ala Arg Lys Phe Ser Tyr
```

```
                290             295             300
Gly Thr Cys Val Arg Pro Val Val Tyr Gly Val Ser Thr Gly
305             310             315             320

Tyr Gln Ile Arg Glu Ile Ser Arg Gly Cys Asn Val Leu Cys Gly Thr
                325             330             335

Pro Gly Arg Leu Leu Asp Val Ile Gly Arg Gly Lys Ile Gly Leu Ser
                340             345             350

Lys Leu Arg Tyr Phe Val Leu Asp Glu Ala Asp Arg Met Leu Asp Met
                355             360             365

Gly Phe Glu Pro Asp Met Arg Arg Leu Val Gly Ser Pro Gly Met Pro
370             375             380

Thr Lys Glu His Arg Gln Thr Leu Met Phe Ser Ala Thr Tyr Pro Glu
385             390             395             400

Asp Ile Gln Arg Met Ala Ala Asp Phe Leu Lys Thr Asp Tyr Leu Phe
                405             410             415

Leu Ala Val Gly Val Val Gly Gly Ala Cys Ser Asp Val Glu Gln Thr
                420             425             430

Phe Val Gln Val Thr Lys Phe Ser Lys Arg Glu Gln Leu Leu Asp Leu
                435             440             445

Leu Lys Thr Thr Gly Thr Glu Arg Thr Met Val Phe Val Glu Thr Lys
450             455             460

Arg Gln Ala Asp Phe Ile Ala Thr Tyr Leu Cys Gln Glu Lys Val Pro
465             470             475             480

Thr Thr Ser Ile His Gly Asp Arg Glu Gln Arg Glu Arg Glu Gln Ala
                485             490             495

Leu Ala Asp Phe Arg Ser Gly Lys Cys Pro Val Leu Val Ala Thr Ser
                500             505             510

Val Ala Ala Arg Gly Leu Asp Val Pro Asp Val Leu Asn Val Val Ser
                515             520             525

Phe Asp Leu Pro Asn Asn Ile Asp Glu Tyr Val His Arg Ile Gly Arg
                530             535             540

Thr Gly Arg Cys Gly Asn Thr Gly Arg Ala Val Ser Phe Tyr Asp Pro
545             550             555             560

Asp Ala Asp Gly Gln Leu Ala Arg Ser Leu Val Thr Ile Leu Ser Lys
                565             570             575

Ala Gln Gln Glu Val Pro Ser Trp Leu Glu Glu Tyr Ala Phe Ser Val
                580             585             590

Pro Gly Asp Ala Gly Phe Asn Ser Ser Lys Arg Asn Phe Ala Ser Ser
                595             600             605

Asp Ser Arg Lys Gly His His Gly Gly Ser Phe Gln Asp Asn Gly Ala
610             615             620

Thr Ser Gln Pro Ala Ala Gln Ala Ala Ala Asp Asp Asp Trp Glu
625             630             635             640

<210> SEQ ID NO 11
<211> LENGTH: 26
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (1)..(26)
<223> OTHER INFORMATION: n indicates any

<400> SEQUENCE: 11
tayrwbaagc cbacncchgt ncagaa                                        26
```

<210> SEQ ID NO 12
<211> LENGTH: 26
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (1)..(26)
<223> OTHER INFORMATION: n indicates any

<400> SEQUENCE: 12
tchtcdgggw angtrgcrct gaacat                                          26

<210> SEQ ID NO 13
<211> LENGTH: 25
<212> TYPE: DNA
<213> ORGANISM: Artificial
<220> FEATURE:
<223> OTHER INFORMATION: primer

<400> SEQUENCE: 13
tggcaaactt cctggcctcc aggta                                           25

<210> SEQ ID NO 14
<211> LENGTH: 25
<212> TYPE: DNA
<213> ORGANISM: Artificial
<220> FEATURE:
<223> OTHER INFORMATION: primer

<400> SEQUENCE: 14
tctaccaggg agctcatcaa ccaga                                           25

<210> SEQ ID NO 15
<211> LENGTH: 28
<212> TYPE: DNA
<213> ORGANISM: Artificial
<220> FEATURE:
<223> OTHER INFORMATION: primer

<400> SEQUENCE: 15
tccaccatga tgtcatcata cttgtcaa                                        28

<210> SEQ ID NO 16
<211> LENGTH: 25
<212> TYPE: DNA
<213> ORGANISM: Artificial
<220> FEATURE:
<223> OTHER INFORMATION: primer

<400> SEQUENCE: 16
tgcaactcag gtcaatgctg tgtgg                                           25

<210> SEQ ID NO 17
<211> LENGTH: 1090
<212> TYPE: DNA
<213> ORGANISM: Bluefin tuna

<400> SEQUENCE: 17
agggagctca tcaaccagat ttacctggag gccaggaagt tgcctttgg  gacatgtgtg     60 cgtccagtgg tggtttatgg tggagtcagc actggacacc aaataagaga atcgaaagg     120 ggatgcaatg tagtgtgtgg aacaccaggg aggctattgg atatgattgg aagaggaaag    180
gttgggttga gtaagctgcg gtacttggtg ctagatgagg ccgaccggat gttggatatg    240

```
ggatttgagc ctgacatgcg ccgcctggtg ggctcacctg gaatgccatc caaagagaac      300
cgtcagactc tgatgttcag tgccacatac cctgaagaca tccagaggat ggcggctgac      360
ttcctcaaga cagactattt gttcctggct gtgggtgtgg tgggtggagc ctgcagtgat      420
gtggagcaga catttatcca agtcacaaag ttctccaaga gagagcagct ccttgacctc      480
ctgaagacca ctggaacgga gcgcaccatg gtgtttgtag agaccaaacg acaagctgat      540
tttattgcca cgttcttgtg ccaagagaaa gttccaacta ccagcattca cggtgaccga      600
gagcagcggg agcgagagca ggctctggca gacttccgct ctggtaaatg tccagtccta      660
gtagcaacct ctgtagctgc ccgcggtctg gatattccag atgtacagca tgtggttaac      720
tttgacctcc ccaacaacat tgatgaatat gtccaccgta ttgggaggac tggccgctgc      780
ggtaacacag ggagggcagt gtctttctat gaccctgatg ctgatggcca actggctcgc      840
tccttggtca cagtcctgtc caaggcccag caggaagtgc cttcatggtt agaagagtct      900
gcgttcagcg gacctgctac cactggcttt aaccccaccta ggaagaactt tgcctccaca      960
gactccagga agaggatc tttccaagac aacagtgtga agagccagcc ggctgttcag      1020
actgcagcgg atgatgatga ggaatgggaa tagaggagca gcacacccac acagcattga      1080
cctgagttgc                                                             1090

<210> SEQ ID NO 18
<211> LENGTH: 1267
<212> TYPE: DNA
<213> ORGANISM: Nibea mitsukurii

<400> SEQUENCE: 18
tattgctccg ctggacggga tctaatggcc tgcgctcaga ccggatctgg taaaacggct       60
gcgttcctgc tccccattct gcagcagctg atggcggacg gcgtggcagc cagctccttc      120
agcgagctgc aggagcctga agtcctcgtc gtggccccaa ccagggagct catcaaccag      180
atttacatgg aggcccggaa gttctcctat gggacatgcg tgcgtccagt agtggtttat      240
ggcggagtta gcaccggata ccaaatacgg gaaatctcaa gggggtgcaa tgtgctgtgt      300
ggaacaccgg ggagactgtt ggacgtgatt ggaagaggaa agattggctt gagcaagctg      360
cggtactttg tgctggacga ggctgaccgc atgttggaca tgggcttcga accggacatg      420
cgccgtctgg tgggctcccc cggcatgccg accaaagagc accgccagac cctgatgttc      480
agtgccacgt accccgagga catccagagg atggctgctg acttcctgaa gaccgactat      540
ttgttcttgg ccgtgggtgt ggtgggcgga gcctgcagtg acgtggagca gacatttgtc      600
caggtcacaa agttctccaa gagggagcaa ctcctcgacc tcctgaagac aactgggaac      660
ggagcgcacc atggtgtttg tggagaccaa gaggcaagct gatttcatcg cgacgtacct      720
gtgccaggag aaagttccaa caaccagcat tcatggcgac cgtgagcagc gcgagcggga      780
gcaggctctg gcggacttcc gctccggcaa gtgtccggtc ctggtggcga cctccgtagc      840
tgcccgcggc ctggatgttc ccgacgtact gaacgtagtg agctttgacc tccccaacaa      900
catcgacgaa tatgtccacc gcattgggag gaccggccgc tgcgggaaca ctggcagagc      960
cgtgtctttc tatgcccag atgctgatgg gcagctggct cgctcgctcg tcacaatcct      1020
gtccaaggcc cagcaggaag tgccctcgtg gttagaagag tatgcgttca gcgtcccggg      1080
tgacgcgggc ttcaactcct ccaagaggaa cttttgcctcc tcagactcca ggaagggtca      1140
tcatggagga tcttttcagg acaacggtgc gacgagccag ccggccgctc aggccgcggc      1200
tgacgacgat gactgggagt agaggggata tgaacagcag accgccacac atccgtgacc      1260
```

```
tgagttg                                                            1267

<210> SEQ ID NO 19
<211> LENGTH: 24
<212> TYPE: DNA
<213> ORGANISM: Artificial
<220> FEATURE:
<223> OTHER INFORMATION: primer

<400> SEQUENCE: 19
atggtgtttg tagagaccaa acga                                           24

<210> SEQ ID NO 20
<211> LENGTH: 23
<212> TYPE: DNA
<213> ORGANISM: Artificial
<220> FEATURE:
<223> OTHER INFORMATION: primer

<400> SEQUENCE: 20
ccttggacag gactgtgacc aag                                            23

<210> SEQ ID NO 21
<211> LENGTH: 24
<212> TYPE: DNA
<213> ORGANISM: Artificial
<220> FEATURE:
<223> OTHER INFORMATION: primer

<400> SEQUENCE: 21
cggtctggat attccagatg taca                                           24

<210> SEQ ID NO 22
<211> LENGTH: 24
<212> TYPE: DNA
<213> ORGANISM: Artificial
<220> FEATURE:
<223> OTHER INFORMATION: primer

<400> SEQUENCE: 22
ttggacagga ctgtgaccaa ggag                                           24

<210> SEQ ID NO 23
<211> LENGTH: 348
<212> TYPE: DNA
<213> ORGANISM: Scomber

<400> SEQUENCE: 23
atggtgtttg tggagaccaa acgacaagct gattttatcg ccacgttctt gtgccaggag    60
aaagttccaa ccactagcat tcatggtgat cgagagcagc gggagcgaga gcaagctctg   120
gcagacttcc gctctggtaa atgtccagtc atggtggcaa cctctgtagc tgcacgtggt   180
ctggatattc cagatgtaca gcatgtggtg aactttgacc tccccaacaa cattgatgaa   240
tatgttcacc gtattgggag aactggccgc tgcggtaata ctgggagggc agtgtctttc   300
tatgaccctg atggtgatag ccaactggct agctccttgg tcacagtc                348

<210> SEQ ID NO 24
<211> LENGTH: 360
<212> TYPE: DNA
<213> ORGANISM: Euthynnus affinis

<400> SEQUENCE: 24
atggtgtttg tggagaccaa acgacaagct gattttattg ccactttctt gtgccaggag    60
```

```
aaagttccaa ctaccagcat tcatggtgac agagagcagc gggagcgaga gcaggctctg      120
gcagacttcc gctccggtaa atgtcccgtc ctagtggcaa catctgtagc tgcccgcggt      180
ctggatattc cagatgtgca gcatgtggtg aactttgacc tccccaacaa cattgatgaa      240
tatgtccacc gtattgggag aaccggccgc tgcggtaaca ctgggagggc agtgtctttt      300
tatgaccctg atgctgatgg ccaactggct cgctccttgg tcacagtgcg caatagatcc      360
```